(12) United States Patent
Brentzel, Jr. et al.

(10) Patent No.: US 9,925,151 B2
(45) Date of Patent: *Mar. 27, 2018

(54) CLADRIBINE REGIMEN FOR TREATING MULTIPLE SCLEROSIS

(75) Inventors: H. James Brentzel, Jr., Marshfield, MA (US); Maria Lopez-Bresnahan, Lincoln, MA (US); Nazih Ammoury, Prevessin-Moens (FR)

(73) Assignee: MERCK SERONO SA, Coinsins, Vaud (CH)

( * ) Notice: Subject to any disclaimer, the term of this patent is extended or adjusted under 35 U.S.C. 154(b) by 1350 days.

This patent is subject to a terminal disclaimer.

(21) Appl. No.: 12/301,083

(22) PCT Filed: May 23, 2007

(86) PCT No.: PCT/EP2007/055013
§ 371 (c)(1),
(2), (4) Date: Nov. 17, 2008

(87) PCT Pub. No.: WO2007/135172
PCT Pub. Date: Nov. 29, 2007

(65) Prior Publication Data
US 2010/0021429 A1 Jan. 28, 2010

Related U.S. Application Data

(60) Provisional application No. 60/845,470, filed on Sep. 18, 2006.

(30) Foreign Application Priority Data

May 24, 2006 (EP) ................................. 06114537

(51) Int. Cl.
*A61K 31/7076* (2006.01)
*A61K 31/7056* (2006.01)
*A61K 31/00* (2006.01)
*A61K 9/20* (2006.01)
*A61K 38/21* (2006.01)

(52) U.S. Cl.
CPC .............. *A61K 31/00* (2013.01); *A61K 9/205* (2013.01); *A61K 9/2013* (2013.01); *A61K 9/2018* (2013.01); *A61K 31/7056* (2013.01); *A61K 38/215* (2013.01)

(58) Field of Classification Search
None
See application file for complete search history.

(56) References Cited

U.S. PATENT DOCUMENTS

| | | | |
|---|---|---|---|
| 4,588,585 A | 5/1986 | Mark et al. | |
| 4,737,462 A | 4/1988 | Mark et al. | |
| 4,738,931 A | 4/1988 | Sugano et al. | |
| 4,879,111 A | 11/1989 | Chong | |
| 4,904,584 A | 2/1990 | Shaw | |
| 4,959,314 A | 9/1990 | Mark et al. | |
| 4,964,848 A | 10/1990 | Bloom | |
| 4,965,195 A | 10/1990 | Namen et al. | |
| 5,017,691 A | 5/1991 | Lee et al. | |
| 5,106,837 A | 4/1992 | Carson et al. | |
| 5,116,943 A | 5/1992 | Koths et al. | |
| 5,155,027 A | 10/1992 | Sledziewski et al. | |
| 5,208,327 A | 5/1993 | Chen | |
| 5,310,732 A | 5/1994 | Carson et al. | |
| 5,506,213 A | 4/1996 | Carson et al. | |
| 5,506,214 A | 4/1996 | Beutler | |
| 5,541,087 A | 7/1996 | Lo et al. | |
| 6,013,253 A | 1/2000 | Martin et al. | |
| 6,194,395 B1 | 2/2001 | Schultz et al. | |
| 7,177,411 B1 | 2/2007 | Collette | |
| 7,713,947 B2 * | 5/2010 | De Luca et al. | 514/46 |
| 8,377,903 B2 | 2/2013 | De Luca et al. | |
| 2010/0021429 A1 | 1/2010 | Brentzel et al. | |
| 2010/0203017 A1 | 8/2010 | De Luca et al. | |

FOREIGN PATENT DOCUMENTS

| | | |
|---|---|---|
| EP | 0 173 059 | 3/1986 |
| EP | 0 227 110 | 7/1987 |
| EP | 0 526 452 | 2/1993 |
| EP | 0 626 853 B1 | 4/2000 |
| WO | WO 92/13095 | 8/1992 |
| WO | WO 96/19229 | 6/1996 |
| WO | WO 96/19230 | 6/1996 |
| WO | WO 97/24137 | 7/1997 |
| WO | WO 99/55377 | 11/1999 |
| WO | WO 00/23472 | 4/2000 |
| WO | WO 00/64198 | 10/2000 |
| WO | WO 01/03737 | 1/2001 |
| WO | WO 2004/028462 | 4/2004 |
| WO | WO 2004/039363 | 5/2004 |

(Continued)

OTHER PUBLICATIONS

Liliemark et al (Jour Pharm Biomed Anal 13: 661-665, 1995).*
Jacobs et al (Ann Neurol 39: 285-294, 1996).*
Comi and Martino (Clin Neurol Neurosurg 108: 339-345, 2006).*
Rieckmann et al J Neurol 251: 1329-1339, 2004.*
Rieckmann et al. Therap Adv Neurol Disorders 1: 181-192, 2008.*
Smith et al (Mult Scl 11: 573-582, 2005).*
Leary, S. M. "Current Management of Multiple Sclerosis" *Int. J. Clin. Pract.*, 2000, pp. 161-169, vol. 54, No. 3, XP-008018314.
Panitch, H. et al. "Benefits of high-dose, high-frequency interferon beta-1a in relapsing-remitting multiple sclerosis are sustained to 16 months: Final comparative results of the Evidence trial" *Journal of the Neurological Sciences*, 2005, pp. 67-74, vol. 239.
Beutler, E. et al. "Marrow Suppression Produced by Repeated Doses of Cladribine", *Acta Haematol*, 1994, pp. 10-15, vol. 91.

(Continued)

*Primary Examiner* — Daniel E Kolker
*Assistant Examiner* — Aditi Dutt
(74) *Attorney, Agent, or Firm* — Saliwanchik, Lloyd & Eisenschenk

(57) ABSTRACT

The present invention relates to the use of multiple doses of Cladribine combined with beta interferon for the treatment of multiple sclerosis in patients who are refractory to at least one conventional therapy.

40 Claims, No Drawings

(56) References Cited

FOREIGN PATENT DOCUMENTS

| WO | WO 2004/075903 | 9/2004 |
|---|---|---|
| WO | WO 2004/087100 | 10/2004 |
| WO | WO 2004/087101 | 10/2004 |
| WO | WO 2004/096263 | 11/2004 |
| WO | WO 2006/067141 | 6/2006 |

OTHER PUBLICATIONS

Beutler, E. et al. "Treatment of Multiple Sclerosis and Other Autoimmune Diseases With Cladribine", *Seminars in Hematology*, Jan. 1, 1996, pp. 45-52, vol. 33, No. 1, Supplement 1.

Beutler, E. et al. "The treatment of chronic progressive multiple sclerosis with cladribine", *Proc. Natl. Acad. Sci. USA*, Feb. 1996, pp. 1716-1720, vol. 93.

Ellison, G. et al. "Oral Cladribine for Multiple Sclerosis", *Neurology*, Mar. 1997, P03.070, pp. A174-A175, vol. 48, No. 3, XP008047069.

Grieb, P. et al. "Effect of Repeated Treatments with Cladribine (2-Chlorodeoxyadenosine) on Blood Counts in Multiple Sclerosis Patients", *Archivum Immunologiae et Therapiae Experimentalis*, 1995, pp. 323-327, vol. 43, No. 5-6.

Kazimierczuk, Z. et al. "Synthesis of 2'-Deoxytubercidin, 2'-Deoxyadenosine, and Related 2'-Deoxynucleosides via a Novel Direct Stereospecific Sodium Salt Glycosylation Procedure", *J. Am. Chem. Soc.*, 1984, pp. 6379-6382, vol. 106, No. 21.

Kurtzke, J. "Rating neurologic impairment in multiple sclerosis: An expanded disability status scale (EDSS)", *Neurology*, Nov. 1983, pp. 1444-1452, vol. 33.

Langtry, H. et al. "Cladribine: A Review of its Use in Multiple Sclerosis", *Biodrugs*, May 1998, pp. 419-433, vol. 9, No. 3.

Lassmann, H. et al. "Heterogeneity of multiple sclerosis pathogenesis: implications for diagnosis and therapy", *TRENDS in Molecular Medicine*, Mar. 2001, pp. 115-121, vol. 7, No. 3.

Lublin, F. et al. "Defining the clinical course of multiple sclerosis: Results of an international survey", *Neurology*, Apr. 1996, pp. 907-911, vol. 46.

Lucchinetti, C. et al. "Multiple sclerosis: recent developments in neuropathology, pathogenesis, magnetic resonance imaging studies and treatment", *Current Opinion in Neurology*, 2001, pp. 259-269, vol. 14.

Mattson, D. "Update on the diagnosis of multiple sclerosis", *Expert Review of Neurotherapeutics*, May 2002, pp. 319-327, vol. 2, No. 3.

McDonald, W. et al. "Recommended Diagnostic Criteria for Multiple Sclerosis: Guidlines from the International Panel on the Diagnosis of Multiple Sclerosis", *Annals of Neurology*, Jul. 2001, pp. 121-127, vol. 50, No. 1.

Miller, R. et al. "Therapeutic advances in ALS", *Neurology*, 1996, pp. S217, vol. 47, Suppl. 4.

Noseworthy, J. et al. "Multiple Sclerosis", *The New England Journal of Medicine*, Sep. 28, 2000, pp. 938-952, vol. 343, No. 13.

Poser, C. et al. "New Diagnostic Criteria for Multiple Sclerosis: Guidelines for Research Protocols", *Annals of Neurology*, Mar. 1983, pp. 227-231, vol. 13, No. 3.

Rice, G. et al. "Cladribine and progressive MS: Clinical and MRI outcomes of a multicenter controlled trial", *Neurology*, Mar. 2000, pp. 1145-1155, vol. 54.

Romine, J. et al. "A Double-Blind, Placebo-Controlled, Randomized Trial of Cladribine in Relapsing-Remitting Multiple Sclerosis", *Proceedings of the Association of American Physicians*, Jan./Feb. 1999, pp. 35-44, vol. 111, No. 1.

Schumacher, G. et al. "Problems of Experimental Trials of Therapy in Multiple Sclerosis: Report by the Panel on the Evaluation of Experimental Trials of Therapy in Multiple Sclerosis", *Annals New York Academy of Sciences*, Mar. 31, 1965, pp. 552-568, vol. 122.

Selby, R. et al. "Safety and Tolerability of Subcutaneous Cladribine Therapy in Progressive Multiple Sclerosis", *Can J. Neurol. Sci.*, 1998, pp. 295-299, vol. 25.

Sipe, J. et al. "A neurologic rating scale (NRS) for use in multiple sclerosis", *Neurology*, Oct. 1984, pp. 1368-1372, vol. 34.

Stelmasiak, Z. et al. "A pilot trial of cladribine (2-chlorodeoxyadenosine) in remitting-relapsing multiple sclerosis", *Med. Sci Monit.*, 1998, pp. 4-8, vol. 4, No. 1.

Office Action dated Aug. 3, 2009 in U.S. Appl. No. 11/722,018, filed Jun. 18, 2007.

Office Action dated Dec. 19, 2011 in U.S. Appl. No. 12/766,173, filed Apr. 23, 2010.

Final Office Action dated May 24, 2012 in U.S. Appl. No. 12/766,173, filed Apr. 23, 2010.

Notice of Allowance dated Oct. 23, 2012 in U.S. Appl. No. 12/766,173, filed Apr. 23, 2010.

Response Under 37 C.F.R. §1.116 dated Aug. 24, 2012 in U.S. Appl. No. 12/766,173, filed Apr. 23, 2010.

Giovannoni, G. et al. "A Placebo-Controlled Trial of Oral Cladribine for Relapsing Multiple Sclerosis" *The New England Journal of Medicine*, Jan. 20, 2010, pp. 1-11.

Lublin, F. D. et al. "Randomized Study Combining Interferon & Glatiramer Acetate in Multiple Sclerosis" *Annals of Neurology*, Mar. 2013, pp. 1-24, vol. 73, No. 3.

Montalban, X. et al. "Phase II randomized study of oral cladribine added to interferon-beta in patients with active relapsing disease" *Clinical Study Report*, p. 1.

Murdoch, D. et al. "Subcutaneous Recombinant Interferon-β-1a (Rebif®): A Review of its Use in Relapsing-Remitting Multiple Sclerosis" *Drugs*, 2005, pp. 1295-1312, vol. 65, No. 9.

Springer [online], retrieved on Nov. 15, 2013, retrieved from the internet, URL: http://link.springer.com/aricle/10.2165%2F00003495-200565090-00010, Murdoch, D. et al. Subcutaneous Recombinant Interfereon-β-1a (Rebif®), pp. 1-2, summary only, 2005.

Evans, A. C. et al. "The Role of MRI in Clinical Trials of Multiple Sclerosis: Comparison of Image Processing Techniques" American Neurological Association, Jan. 1997, pp. 125-132, vol. 41, No. 1.

Sipe, J. C. et al. "Cladribine in treatment of chronic progressive multiple sclerosis" *The Lancet*, Jul. 2, 1994, pp. 9-13, vol. 344.

Shin-Yakuzaigaku-Souron (revised 3$^{rd}$ edition), Introduction to Modern Pharmaceutics, Chapter 8, *Nankodo Co. Ltd.*, Apr. 10, 1987, pp. 240-247. Teisuke Okano.

Carson, D.A. et al. "Antileukemic and immunosuppressive activity of 2-chloro-2'-deoxyadenosine" *Proc. Natl. Acad. Sci. USA*, Apr. 1984, pp. 2232-2236, vol. 81.

\* cited by examiner

SEQUENCE LISTING

```
<160> NUMBER OF SEQ ID NOS: 1

<210> SEQ ID NO 1
<211> LENGTH: 13
<212> TYPE: PRT
<213> ORGANISM: Artificial sequence
<220> FEATURE:
<223> OTHER INFORMATION: amino acid linker sequence

<400> SEQUENCE: 1

Glu Phe Gly Ala Gly Leu Val Leu Gly Gly Gln Phe Met
1               5                   10
```

CLADRIBINE REGIMEN FOR TREATING MULTIPLE SCLEROSIS

CROSS-REFERENCE TO RELATED APPLICATION

This application is the U.S. national stage application of International Patent Application No. PCT/EP2007/055013, filed May 23, 2007, which claims the benefit of U.S. Provisional Patent Application No. 60/845,470, filed Sep. 18, 2006, the disclosures of which are hereby incorporated by reference in their entireties, including all figures, tables and amino acid or nucleic acid sequences.

FIELD OF THE INVENTION

The present invention relates to the use of multiple doses of Cladribine combined with beta interferon for the treatment of multiple sclerosis in patients who are refractory to at least one conventional therapy for MS.

BACKGROUND OF THE INVENTION

Multiple sclerosis (MS) is the most known chronic inflammatory demyelinating disease of the central nervous system in humans. The onset of the disease typically occurs during ages 20 to 40. Women are affected approximately twice as often as men.

Over time, MS may result in the accumulation of various neurological disabilities. Clinical disability in MS is presumed to be a result of repeated inflammatory injury with subsequent loss of myelin and axons, leading to tissue atrophy.

MS is manifested in physical symptoms (relapses and disability progression), Central Nervous System (CNS) inflammation, brain atrophy and cognitive impairment. Presenting symptoms include focal sensory deficits, focal weakness, visual problems, imbalance and fatigue. Sexual impairment and sphincter dysfunction may occur. Approximately half of the patients with MS may experience cognitive impairment or depression.

MS is now considered to be a multi-phasic disease and periods of clinical quiescence (remissions) occur between exacerbations. Remissions vary in length and may last several years but are infrequently permanent.

Four courses of the disease are individualized: relapsing-remitting multiple sclerosis (RRMS), secondary progressive multiple sclerosis (SPMS), primary progressive multiple sclerosis (PPMS) and progressive relapsing multiple sclerosis (PRMS).

More than 80% of patients with MS will initially display a RRMS course with clinical exacerbation of neurological symptoms, followed by a recovery that may or may not be complete (Lublin and Reingold, *Neurology*, 1996, 46:907-911).

During RRMS, accumulation of disability results from incomplete recovery from relapses. Approximately, half of the patients with RRMS switch to a progressive course, called SPMS, 10 years after the diseased onset. During the SP phase, worsening of disability results from the accumulation of residual symptoms after exarcerbation but also from insidious progression between exacerbations (Lublin and Reingold above). 10% of MS patients have PPMS which is characterized by insidious progression of the symptoms from the disease onset. Less than 5% of patients have PRMS and are often considered to have the same prognosis as PPMS. It is suggested that distinct pathogenic mechanisms may be involved in different patient sub-groups and have wide-ranging implications for disease classification (Lassmann et al., 2001, *Trends Mol. Med.*, 7, 115-121; Lucchinetti et al., *Curr. Opin. Neurol.*, 2001, 14, 259-269).

MS onset is defined by the occurrence of the first neurological symptoms of CNS dysfunction. Advances in cerebrospinal fluid (CSF) analysis and magnetic resonance imaging (MRI) have simplified the diagnostic process and facilitated early diagnostic (Noseworthy et al., *The New England Journal of Medicine*, 2000, 343, 13, 938-952). The International Panel on the Diagnosis of MS issued revised criteria facilitating the diagnosis of MS and including MRI together with clinical and para-clinical diagnostic methods (McDonald et al., 2001, *Ann. Neurol.*, 50:121-127).

Current medications for MS which are disease modifying treatments, i.e. modifying the course of MS, modulate or suppress the immune system. There are four FDA approved immunomodulating agents for RRMS: three beta interferons (Betaseron®, Berlex; Avonex®, Biogen; Rebif®, Serono) and Glatimarer Acetate (Copaxone®, Teva). There is also one FDA approved immunosuppressing drug for worsening MS, Mitoxantrone (Novantrone®, Serono). Several other immunosuppressive agents are used, although not FDA approved.

Among them, Cladribine, a chlorinated purine analogue 2-chloro-2'deoxyadenosine (2-CdA), has been suggested to be useful in the treatment of MS (EP 626853B1 and U.S. Pat. No. 5,506,214).

Several clinical studies with Cladribine in patients with multiple sclerosis have investigated the use of i.v. and s.c. Cladribine in MS.

Two double-blind, placebo controlled Phase II studies were conducted respectively in the treatment of Chronic Progressive MS (Selby et al., 1998, *Can. J. Neurol. Sci.*, 25:295-299) and Relapsing-Remitting MS respectively (Romine et al., 1999, *Proceedings of the Association of American Physicians*, 111, 1, 35-44).

In the first trial, the Cladribine dose used was 0.1 mg/kg/day for 7 days by continuous i.v. infusion. The treatment for repeated for 4 consecutive months.

In the second clinical trial, the Cladribine dose used was 0.07 mg/kg/day for 5 days by subcutaneous injection. The treatment was repeated for 6 consecutive months.

In addition, placebo controlled Phase III study was conducted in patients with primary progressive (PP) or secondary progressive (SP) multiple sclerosis (Rice at al., 2000, *Neurology*, 54, 5, 1145-1155). In this study, both patient groups received Cladribine by subcutaneous injection at a dose of 0.07 mg/kg/day. The treatment was repeated for either 2 months or 6 months.

The Phase II clinical studies provided evidence for the positive effects of Cladribine in patients with MS in terms of Kutzke Extended Disability Status Scale (EDSS), Scripps Neurologic rating Scale (SNRS) scores and Magnetic Resonance Imaging (MRI) findings (Beutler et al., 1996, *Proc. Nat. Acad. Sci. USA*, 93, 1716-1720; Romine et al., 1999 above). Phase III study results, were positive on the significant reduction of MRI-measured brain lesions (Rice at al., 2000, above).

Some adverse effects (AEs), such as increased incidence of infections related to compromised immune function or myelosuppression, were observed with the highest doses (Selby et al., 1998, above; Beutler et al., 1994, *Acta hematol.*, 91:10-15). Due to the narrow margin of safety between the efficacy dose and the dose of occurrence of AEs, to date, all clinical trials for Cladribine in multiple sclerosis have been conducted using either i.v. or s.c. administration. As a result, Beutler et al. (Beutler et al., 1996, *Seminars in Hematology*, 33, 1(SI), 45-52) excluded the oral route for the treatment of multiple sclerosis with Cladribine.

Grieb et al. reported a small trial in 11 patients with remitting-relapsing multiple sclerosis (Grieb et al., 1995, *Archivum Immunologiae et Therapiae Experimentalis*, 43 (5-6), 323-327) wherein Cladribine has been orally administered during 6 monthly courses of 5 days at a total dose of about 4-5.7 mg/kg (patients of about 52 and about 75 kilos, respectively) i.e. a total effective dose of 2-2.85 mg/kg. For some patients, a single re-treatment of 5 days was performed at a cumulative dose of 0.4-0.66 mg/kg after a cladribine free-period of 3 or 6 months. The side effects observed with the regimen above were said to be less severe than the ones observed in the study on patients suffering from chronic progressive multiple sclerosis treated by i.v. infusion of Cladribine (Sipe et al., 1994, *Lancet*, 344, 9-13) but were still present. In addition, the therapeutic efficacy of the oral regimen above versus the i.v. infusion therapy was questioned (Grieb et al., 1995, above) and a group of "non-responders" has been identified (Stelmasiak et al., 1998, *Laboratory Investigations*, 4(I), 4-8).

Therefore, it would be desirable to have a method for treating multiple sclerosis comprising the oral administration of Cladribine that would permit the same or improved effect on MS lesions while decreasing the occurrence and/or severity adverse events. In addition, as MS is a chronic disease, it would be desirable to decrease the occurrence and/or severity adverse events in such a way that re-treatments are possible. A sustained benefit of Cladribine treatment between the treatment periods is also desirable.

It would also be desirable to have a method for treating multiple sclerosis that would permit the treatment of patients who are refractory to at least one conventional therapy.

SUMMARY OF THE INVENTION

The present invention is directed towards the use of Cladribine combined with beta interferon for the preparation of a pharmaceutical formulation for the treatment of multiple sclerosis, wherein the Cladribine preparation is to be the orally administered.

Particularly, the invention is directed towards the use of Cladribine combined with beta interferon for the preparation of a medicament for the treatment of patients who are refractory to at least one conventional therapy.

An embodiment of the invention provides an improved dosing regimen for Cladribine combined with beta interferon in the treatment of multiple sclerosis.

An additional embodiment of the invention provides the use of Cladribine combined with beta interferon for the preparation of a pharmaceutical formulation for the treatment of multiple sclerosis wherein adverse effects are reduced, allowing further use of Cladribine.

In one embodiment, the invention provides:

1. The use of a combination of Cladribine and IFN-beta for the manufacture of a medicament for treating patients suffering from multiple sclerosis and who are refractory to at least one conventional therapy for multiple sclerosis, wherein Cladribine is to be orally administered following the sequential steps below:
   (i) An induction period wherein Cladribine is administered and wherein the total dose of Cladribine reached at the end of the induction period is from about 1.7 mg/kg to about 3.5 mg/kg;
   (ii) A Cladribine-free period wherein no Cladribine is administered;
   (iii) A maintenance period wherein Cladribine is administered and wherein the total dose of Cladribine administered during the maintenance period is lower than or equal to the total dose of Cladribine reached at the end of the induction period (i);
   (iv) A Cladribine-free period wherein no Cladribine is administered.

In another embodiment, the invention provides:

2. The use of a combination of Cladribine and IFN-beta for treating patients suffering from multiple sclerosis and who are refractory to at least one conventional therapy for multiple sclerosis, comprising the oral administration of Cladribine following the sequential steps below:
   (i) An induction period wherein Cladribine is administered and wherein the total dose of Cladribine reached at the end of the induction period is from about 1.5 mg/kg to about 3.5 mg/kg;
   (ii) A Cladribine-free period wherein no Cladribine is administered;
   (iii) A maintenance period wherein Cladribine is administered and wherein the total dose of Cladribine administered during the maintenance period is lower than or equal to the total dose of Cladribine reached at the end of the induction period (i);
   (iv) A Cladribine-free period wherein no Cladribine is administered.

In another embodiment, the invention provides:

3. A product comprising Cladribine and IFN-beta as a combined preparation for simultaneous, separate or sequential use in the therapy of patients suffering from multiple sclerosis and who are refractory to at least one conventional therapy for multiple sclerosis, wherein Cladribine is to be orally administered following the sequential steps below:
   (i) An induction period wherein Cladribine is administered and wherein the total dose of Cladribine reached at the end of the induction period is from about 1.7 mg/kg to about 3.5 mg/kg;
   (ii) A Cladribine-free period wherein no Cladribine is administered;
   (iii) A maintenance period wherein Cladribine is administered and wherein the total dose of Cladribine administered during the maintenance period is lower than or equal to the total dose of Cladribine reached at the end of the induction period (i);
   (iv) A Cladribine-free period wherein no Cladribine is administered.

In another embodiment, the invention provides:

4. The use or product according to point 1, 2 or 3 here above, wherein the induction period lasts up to 4 months, or up to 3 months, or up to 2 months.

In another embodiment, the invention provides:

5. The use or product according to any one of points 1 to 4 here above wherein the induction period lasts up to 2 months and the total dose of Cladribine reached at the end of the induction period is about 1.7 mg/kg, preferably 1.75 mg/kg.

In another embodiment, the invention provides:

6. The use or product according to any one of points 1 to 4 here above wherein the induction period lasts up to 4 months and the total dose of Cladribine reached at the end of the induction period is about 3.5 mg/kg, preferably 3.5 mg/kg.

In another embodiment, the invention provides:

7. The use or product according to any of points 1 to 5 here above wherein the Cladribine-free period (ii) lasts up to 10 months, or up to 9 months, or up to 8 months.

In another embodiment, the invention provides:

8. The use or product according to point 7 here above wherein the Cladribine-free period (ii) lasts 8 months.

In another embodiment, the invention provides:

9. The use or product according to any one of points 1 to 8 here above wherein the Cladribine-free (iv) period lasts up to 10 months.

In another embodiment, the invention provides:

10. The use or product according to any one of points 1 to 9 here above wherein the combined duration of the induction period (i) with the Cladribine-free period (ii) is about 1 year (about 12 months).

In another embodiment, the invention provides:

11. The use or product according to point 10 here above wherein the duration of the induction period is about 4 months and the duration of the Cladribine-free period (ii) is about 8 months, or the duration of the induction period is about 3 months and the duration of the Cladribine-free period (ii) is about 9 months, or the duration of the induction period is about 2 months and the duration of the Cladribine-free period (ii) is about 10 months.

In another embodiment, the invention provides:

12. The use or product according to any one of points 1 to 9 here above wherein the combined duration of the induction period (i) with the Cladribine-free period (ii) is about 1 year (about 12 months) and the total dose of Cladribine reached at the end of this year of treatment is about 1.7 mg/kg, preferably 1.75 mg/kg or about 3.5 mg/kg, preferably 3.5 mg/kg.

In another embodiment, the invention provides:

13. The use or product according to point 12 here above wherein the duration of the induction period is about 4 months and the duration of the Cladribine-free period (ii) is about 8 months, or the duration of the induction period is about 3 months and the duration of the Cladribine-free period (ii) is about 9 months, or the duration of the induction period is about 2 months and the duration of the Cladribine-free period (ii) is about 10 months.

In another embodiment, the invention provides:

14. The use or product according to any one of points 1 to 13 here above wherein the maintenance period lasts up to 4 months, or up to 3 months or up to 2 months.

In another embodiment, the invention provides:

15. The use or product according to any one of points 1 to 14 here above wherein the maintenance period lasts up to 2 months and the total dose of Cladribine administered during the maintenance period is about 1.7 mg/kg, preferably 1.75 mg/kg.

In another embodiment, the invention provides:

16. The use or product according to any one of points 1 to 15 here above wherein the combined duration of the maintenance period (iii) with the Cladribine-free period (iv) is about 1 year (about 12 months).

In another embodiment, the invention provides:

17. The use or product according to point 16 here above wherein the duration of the maintenance period (iii) is about 4 months and the duration of the Cladribine-free period (iv) is about 8 months, or the duration of the maintenance period (iii) is about 3 months and the duration of the Cladribine-free period (iv) is about 9 months.

In another embodiment, the invention provides:

18. The use or product according to point 16 here above wherein the duration of the maintenance period (iii) is about 2 months and the duration of the Cladribine-free period (iv) is about 10 months.

In another embodiment, the invention provides:

19. The use or product according to point 16 here above wherein the combined duration of the maintenance period (iii) with the Cladribine-free period (iv) is about 1 year (about 12 months) and the total dose of Cladribine administered during this year of treatment is about 1.7 mg/kg, preferably 1.75 mg/kg.

In another embodiment, the invention provides:

20. The use or product according to point 19 here above wherein the duration of the maintenance period (iii) is about 4 months and the duration of the Cladribine-free period (iv) is about 8 months, or the duration of the maintenance period (iii) is about 3 months and the duration of the Cladribine-free period (iv) is about 9 months.

In another embodiment, the invention provides:

21. The use or product according to point 19 here above wherein the duration of the maintenance period (iii) is about 2 months and the duration of the Cladribine-free period (iv) is about 10 months.

In another embodiment, the invention provides:

22. The use or product according to any one of points 1 to 21 here above wherein the combined duration of the induction period (i), the Cladribine-free period (ii), the maintenance period (iii) and the Cladribine-free period (iv) is about 2 years (about 24 months).

In another embodiment, the invention provides:

23. The use or product according to point 22 here above wherein:
the duration of the induction period is about 4 months, the duration of the Cladribine-free period (ii) is about 8 months, the duration of the maintenance period (iii) is about 4 months and the duration of the Cladribine-free period (iv) is about 8 months or;
the duration of the induction period is about 4 months, the duration of the Cladribine-free period (ii) is about 8 months, the duration of the maintenance period (iii) is about 3 months and the duration of the Cladribine-free period (iv) is about 9 months, or;
the duration of the induction period is about 4 months, the duration of the Cladribine-free period (ii) is about 8 months, the duration of the maintenance period (iii) is about 2 months and the duration of the Cladribine-free period (iv) is about 10 months, or;
the duration of the induction period is about 3 months, the duration of the Cladribine-free period (ii) is about 9 months, the duration of the maintenance period (iii) is about 4 months and the duration of the Cladribine-free period (iv) is about 8 months, or;
the duration of the induction period is about 3 months, the duration of the Cladribine-free period (ii) is about 9 months, the duration of the maintenance period (iii) is about 3 months and the duration of the Cladribine-free period (iv) is about 9 months, or;
the duration of the induction period is about 3 months, the duration of the Cladribine-free period (ii) is about 9 months, the duration of the maintenance period (iii) is about 2 months and the duration of the Cladribine-free period (iv) is about 10 months, or;
the duration of the induction period is about 2 months, the duration of the Cladribine-free period (ii) is about 10 months, the duration of the maintenance period (iii) is about 4 months and the duration of the Cladribine-free period (iv) is about 8 months, or;
the duration of the induction period is about 2 months, the duration of the Cladribine-free period (ii) is about 10 months, the duration of the maintenance period (iii) is about 3 months and the duration of the Cladribine-free period (iv) is about 9 months, or;

the duration of the induction period is about 2 months, the duration of the Cladribine-free period (ii) is about 10 months, the duration of the maintenance period (iii) is about 2 months and the duration of the Cladribine-free period (iv) is about 10 months.

In another embodiment, the invention provides:

24. The use or product according to point 22 here above wherein the combined duration of the induction period (i) and the Cladribine-free period (ii) is about 1 year (12 months), the combined duration of the maintenance period (iii) and the Cladribine-free period (iv) is about 1 year (about 12 months), the total dose of Cladribine administered during the first year of treatment is about 1.7 mg/kg, preferably 1.75 mg/kg and the total dose of Cladribine administered during the second year of treatment is about 1.7 mg/kg, preferably 1.75 mg/kg.

In another embodiment, the invention provides:

25. The use or product according to point 24 here above wherein:
    the duration of the induction period is about 4 months, the duration of the Cladribine-free period (ii) is about 8 months, the duration of the maintenance period (iii) is about 4 months and the duration of the Cladribine-free period (iv) is about 8 months or;
    the duration of the induction period is about 4 months, the duration of the Cladribine-free period (ii) is about 8 months, the duration of the maintenance period (iii) is about 3 months and the duration of the Cladribine-free period (iv) is about 9 months, or;
    the duration of the induction period is about 4 months, the duration of the Cladribine-free period (ii) is about 8 months, the duration of the maintenance period (iii) is about 2 months and the duration of the Cladribine-free period (iv) is about 10 months, or;
    the duration of the induction period is about 3 months, the duration of the Cladribine-free period (ii) is about 9 months, the duration of the maintenance period (iii) is about 4 months and the duration of the Cladribine-free period (iv) is about 8 months, or;
    the duration of the induction period is about 3 months, the duration of the Cladribine-free period (ii) is about 9 months, the duration of the maintenance period (iii) is about 3 months and the duration of the Cladribine-free period (iv) is about 9 months, or;
    the duration of the induction period is about 3 months, the duration of the Cladribine-free period (ii) is about 9 months, the duration of the maintenance period (iii) is about 2 months and the duration of the Cladribine-free period (iv) is about 10 months, or;
    the duration of the induction period is about 2 months, the duration of the Cladribine-free period (ii) is about 10 months, the duration of the maintenance period (iii) is about 4 months and the duration of the Cladribine-free period (iv) is about 8 months, or;
    the duration of the induction period is about 2 months, the duration of the Cladribine-free period (ii) is about 10 months, the duration of the maintenance period (iii) is about 3 months and the duration of the Cladribine-free period (iv) is about 9 months, or;
    the duration of the induction period is about 2 months, the duration of the Cladribine-free period (ii) is about 10 months, the duration of the maintenance period (iii) is about 2 months and the duration of the Cladribine-free period (iv) is about 10 months.

In another embodiment, the invention provides:

26. The use or product according to point 22 here above wherein the combined duration of the induction period (i) and the Cladribine-free period (ii) is about 1 year (12 months), the combined duration of the maintenance period (iii) and the Cladribine-free period (iv) is about 1 year (about 12 months), the total dose of Cladribine administered during the first year of treatment is about 3.5 mg/kg, preferably 3.5 mg/kg and the total dose of Cladribine administered during the second year of treatment is about 1.7 mg/kg, preferably 1.75 mg/kg.

In another embodiment, the invention provides:

27. The use or product according to point 26 here above wherein:
    the duration of the induction period is about 4 months, the duration of the Cladribine-free period (ii) is about 8 months, the duration of the maintenance period (iii) is about 4 months and the duration of the Cladribine-free period (iv) is about 8 months or;
    the duration of the induction period is about 4 months, the duration of the Cladribine-free period (ii) is about 8 months, the duration of the maintenance period (iii) is about 3 months and the duration of the Cladribine-free period (iv) is about 9 months, or;
    the duration of the induction period is about 4 months, the duration of the Cladribine-free period (ii) is about 8 months, the duration of the maintenance period (iii) is about 2 months and the duration of the Cladribine-free period (iv) is about 10 months, or;
    the duration of the induction period is about 3 months, the duration of the Cladribine-free period (ii) is about 9 months, the duration of the maintenance period (iii) is about 4 months and the duration of the Cladribine-free period (iv) is about 8 months, or;
    the duration of the induction period is about 3 months, the duration of the Cladribine-free period (ii) is about 9 months, the duration of the maintenance period (iii) is about 3 months and the duration of the Cladribine-free period (iv) is about 9 months, or;
    the duration of the induction period is about 3 months, the duration of the Cladribine-free period (ii) is about 9 months, the duration of the maintenance period (iii) is about 2 months and the duration of the Cladribine-free period (iv) is about 10 months, or;
    the duration of the induction period is about 2 months, the duration of the Cladribine-free period (ii) is about 10 months, the duration of the maintenance period (iii) is about 4 months and the duration of the Cladribine-free period (iv) is about 8 months, or;
    the duration of the induction period is about 2 months, the duration of the Cladribine-free period (ii) is about 10 months, the duration of the maintenance period (iii) is about 3 months and the duration of the Cladribine-free period (iv) is about 9 months, or;
    the duration of the induction period is about 2 months, the duration of the Cladribine-free period (ii) is about 10 months, the duration of the maintenance period (iii) is about 2 months and the duration of the Cladribine-free period (iv) is about 10 months.

In another embodiment, the invention provides:

28. The use or product according to any one of points 1 to 27 here above wherein steps (iii) to (iv) are repeated one, two or three times.

In another embodiment, the invention provides:

29. The use or product according to any one of points 1 to 28 here above wherein the induction period lasts during 2 months, the total dose of Cladribine reached at the end of the induction period is 1.75 mg/kg, the Cladribine-free period (ii) lasts during 10 months, the maintenance period lasts during 2 months and the total dose of Cladribine administered during the maintenance period is 1.75 mg/kg, In another embodiment, the invention provides:

30. The use or product according to point 29 here above wherein the Cladribine-free (iv) period lasts during 10 months.

In another embodiment, the invention provides:

31. The use or product to any one of points 1 to 28 here above wherein the induction period lasts during 4 months, the total dose of Cladribine reached at the end of the induction period is 3.5 mg/kg, the Cladribine-free period (ii) lasts during 8 months, the maintenance period lasts during 2 months and the total dose of Cladribine administered during the maintenance period is 1.75 mg/kg, the Cladribine-free (iv) period lasts during 10 months.

In another embodiment, the invention provides:

32. The use or product according to point 31 here above wherein the Cladribine-free (iv) period lasts during 10 months.

In another embodiment, the invention provides:

33. The use or product according to any one of points 1 to 32 here above wherein steps (iii) to (iv) are repeated one time.

In another embodiment, the invention provides:

34. The use or product according to any one of points 1 to 33 here above wherein the bioavailability of Cladribine is of about 40%.

In another embodiment, the invention provides:

35. The use or product according to any one of points 1 to 34 here above wherein the total effective dose of Cladribine reached at the end of the induction period is from about 0.7 mg/kg to about 1.4 mg/kg.

In another embodiment, the invention provides:

36. The use or product according to any one of points 1 to 35 here above wherein the total effective dose of Cladribine reached at the end of the induction period is about 0.7 mg/kg or about 1.4 mg/kg.

In another embodiment, the invention provides:

36. The use or product according to any one of points 1 to 36 here above wherein the total effective dose of Cladribine administered during the maintenance period is about 0.7 mg/kg.

In another embodiment, the invention provides:

37. The use or product according to any one of points 1 to 36 here above wherein Cladribine is administered from 4 to 7 days per month, preferably 4 or 5 days per month, during the induction period.

In another embodiment, the invention provides:

38. The use or product according to point 37 here above wherein Cladribine is administered from day 1 to day 5, or from day 1 to day 4, each month during the induction period.

In another embodiment, the invention provides:

39. The use or product according to point 37 or 38 here above wherein Cladribine is administered at a daily dose of about 0.175 mg/kg during the induction period.

In another embodiment, the invention provides:

40. The use or product according to point 37, 38 or 39 here above wherein Cladribine is administered several times a day during the induction period, preferably twice or three times a day, more preferably twice a day.

In another embodiment, the invention provides:

41. The use or product according to any one of points 1 to 40 here above wherein Cladribine is administered from 4 to 7 days per month, preferably 4 or 5 days per month, during the maintenance period.

In another embodiment, the invention provides:

42. The use or product according to point 41 here above wherein Cladribine is administered from day 1 to day 5, or from day 1 to day 4 each month during the maintenance period.

In another embodiment, the invention provides:

43. The use or product according to points 41 or 42 here above wherein Cladribine is administered at a daily dose of about 0.175 mg/kg during the maintenance period.

In another embodiment, the invention provides:

44. The use or product according to point 41, 42 or 43 here above wherein Cladribine is administered several times a day during the maintenance period, preferably twice or three times a day, more preferably twice a day.

In another embodiment, the invention provides:

45. The use or product according to any one of points 1 to 44 here above wherein IFN-beta is administered simultaneously, separately or sequentially with oral Cladribine.

In another embodiment, the invention provides:

46. The use or product according to point 45 here above wherein IFN-beta is administered before the induction period (i), and/or after the maintenance period (iii).

In another embodiment, the invention provides:

47. The use or product according to point 45 here above wherein IFN-beta is administered during the Cladribine-free period (ii) and/or (iv).

In another embodiment, the invention provides:

48. The use or product according to point 45 here above wherein IFN-beta is administered simultaneously with oral Cladribine.

In another embodiment, the invention provides:

49. The use or product according to point 48 here above wherein IFN-beta is administered during the induction period (i) and/or the maintenance period (iv).

In another embodiment, the invention provides:

50. The use or product according to point 49 here above wherein IFN-beta is administered during the induction period (i), the maintenance period (iv) and the Cladribine-free periods (ii) and (iv).

In another embodiment, the invention provides:

51. The use or product according to point 50 here above wherein IFN-beta is administered before the induction period (i), during the induction period (i), during the maintenance period (iv), during the Cladribine-free periods (ii) and (iv) and after the Cladribine-free period (iv).

In another embodiment, the invention provides:

52. The use or product according to any one of points 1 to 51 wherein the IFN-beta is chosen in the group consisting of: interferon-beta 1a and interferon-beta 1b.

In another embodiment, the invention provides:

53. The use or product according to point 52 here above wherein the IFN-beta is chosen in the group consisting of: Avonex® (Biogen), Rebif® (Serono), and Betaseron® (Berlex/Schering AG).

In another embodiment, the invention provides:

54. The use or product according to point 53 here above wherein the IFN-beta is Rebif® (Serono).

In another embodiment, the invention provides:

55. The use or product according to any one of points 52 to 54 here above wherein the IFN-beta is administered systemically.

In another embodiment, the invention provides:

56. The use or product according to point 55 here above wherein the IFN-beta is administered subcutaneously or intramuscularly.

In another embodiment, the invention provides:

57. The use or product according to point 56 here above wherein the IFN-beta is dosed at least at 44 mcg subcutaneously per administration.

In another embodiment, the invention provides:

58. The use or product according to point 56 here above wherein the IFN-beta regimen is selected from the group consisting of: 12 MIU (44 mcg) of IFN-beta three times a week, 12 MIU (44 mcg) daily, 24 MIU (88 mcg) three times a week and 24 MIU (88 mcg) daily.

In another embodiment, the invention provides:

59. The use or product according to point 56 here above wherein the IFN-beta used is Rebif® (Serono) and is administered at 44 mcg subcutaneously three times a week.

In another embodiment, the invention provides:

60. The use or product according to any one of points 1 to 59 here above wherein the conventional therapy is selected from the group consisting of: treatment with beta interferon, treatment with Glatimarer Acetate (Copaxone®, Teva), treatment with natalizumab (Tysabri®, Biogen/Elan), and treatment with Mitoxantrone (Novantrone®, Serono).

In another embodiment, the invention provides:

61. The use or product according to point 60 here above wherein the conventional therapy is treatment with beta interferon, preferably treatment with Betaseron® (Berlex/Schering AG); Avonex® (Biogen); or Rebif® (Serono).

In another embodiment, the invention provides:

62. The use or product according to point 61 here above wherein the conventional therapy is a treatment with Rebif® (Serono).

In another embodiment, the invention provides:

63. The use or product according to point 60 or 61 here above wherein the patients to be treated are refractory to one, two, three or four of the conventional therapies.

In another embodiment, the invention provides:

64. The use or product according to any one of points 1 to 63 here above wherein the refractory patients to be treated have experienced at least one relapse in spite of receiving at least one conventional therapy.

In another embodiment, the invention provides:

65. The use or product according to point 64 here above wherein the at least one relapse occurred during the year prior the beginning of the treatment according to any of the preceding claims.

In another embodiment, the invention provides:

66. The use or product according to point 65 here above wherein the patients to be treated have experienced at least one relapse during the year preceding the beginning of the treatment according to any of the preceding claims and have been treated with Rebif® (Serono), in particular 12 MIU (44 mcg) of Rebif® three times a week.

In another embodiment, the invention provides:

67. The use or product according to any of the points 1 to 66 here above wherein the refractory patients to be treated have acquired enhanced lesion number or enhanced brain lesion volume in the CNS as detected using methods such as MRI technique, in spite of receiving at least one conventional therapy.

In another embodiment, the invention provides:

68. The use or product according to point 67 here above wherein the enhanced lesion number or enhanced brain lesion volume occurred during the year prior the beginning of the treatment according to any of the preceding claims.

In another embodiment, the invention provides:

69. The use or product according to claim 68 here above wherein the patients to be treated have acquired enhanced lesion number or enhanced brain lesion volume in the CNS during the year preceding the beginning of the treatment according to any of the preceding claims and have been treated with Rebif® (Serono), in particular 12 MIU (44 mcg) of Rebif® three times a week.

In another embodiment, the invention provides:

70. The use or product according to any one of points 1 to 69 here above wherein the refractory patients to be treated have experienced at least one relapse and develop increasing disability because of progressive forms of the disease.

In another embodiment, the invention provides:

71. The use or product according to any one of points 1 to 70 here above wherein the refractory patients to be treated are suffering from worsening MS, in particular secondary progressive, progressive remitting or worsening relapsing-remitting MS.

DETAILED DESCRIPTION OF THE INVENTION

Definitions

The term "multiple sclerosis" within the meaning of the present invention may be defined as in the DSM-IV classification (Diagnosis and Statistical Manual of Inflammatory CNS Disorders, Fourth Edition, American Psychiatric Association, Washington D.C., 1994).

The "total dose" or "cumulative dose" refers to the total dose of Cladribine administered during the treatment, i.e. the dose reached at the end of the treatment that is calculated by adding the daily doses. For example, the total dose of Cladribine corresponding to a treatment of 0.7 mg/kg Cladribine per day during 5 days is 3.5 mg/kg or the total dose of Cladribine corresponding to a treatment of 0.35 mg/kg Cladribine per day during 5 days is 1.7 mg/kg.

"The total effective dose" or "cumulative effective dose" refers to the bioavailable dose of Cladribine after a given administration period, i.e. the bioavailable dose reached at the end of the treatment that is calculated by adding the daily doses reduced by the bioavailability coefficient. For example, the total effective dose of Cladribine corresponding to a treatment of 0.7 mg/kg Cladribine per day during 5 days wherein the bioavailability of Cladribine is of about 40% is 1.4 mg/kg or the total effective dose of Cladribine corresponding to a treatment of 0.35 mg/kg Cladribine per day during 5 days wherein the bioavailability of Cladribine is of about 40% is 0.7 mg/kg.

Typically, the bioavailability of Cladribine or of a Cladribine formulation used in the context of this invention is from about 30% to about 90%, preferably from about 40% to about 60%, such as about 50%.

"A week" refers to a period of time of about 5, about 6 or about 7 days.

"A month" refers to a period of time of about 28, about 29, about 30 or about 31 days.

"Treatment" comprises the sequential succession of an "induction treatment" and at least a "maintenance treatment". Typically, a treatment according to the invention comprises an "induction treatment" and about one or about two or about three maintenance treatments. Typically, a treatment according to the invention is of about 2 years (about 24 months) or about 3 years (about 36 months) or about 4 years (about 48 months).

An "Induction Treatment" consists in the sequential succession of (i) an induction period wherein the Cladribine or the Cladribine pharmaceutical preparation of the invention is orally administered and (ii) a Cladribine-free period. An induction period lasts up to about 4 months or up to about 3 month or up to about 2 months. For example, an induction period lasts for about 2 to about 4 months. An induction period consists in the oral administration of Cladribine or a pharmaceutical preparation thereof during about 1 to about 7 days each month.

A "Cladribine-free period" is a period wherein no Cladribine is administered to the patient. During a Cladribine-free period, the patient can be free of any administration or be dosed with a placebo-pill or another drug except. A Cladribine-free period lasts up to about 10 months or up to 9 months or up to about 8 months. For example, a Cladribine-free period lasts from about 8 to about 10 months, typically at least of about 8 months.

A "Maintenance Treatment" consists in the sequential succession of (i) a maintenance period wherein the Cladribine or the Cladribine pharmaceutical preparation of the invention is orally administered at a lower or equal dose than the Cladribine dose orally administered during the induction treatment and (ii) a Cladribine-free period. A maintenance period lasts for up to about 4 months, or up to about 3 months, or up to about 2 months, preferably up to about 2 months. For example, a maintenance period lasts for about 2 to about 4 months, preferably for about 2 months. A maintenance period consists in the oral administration of Cladribine or of a pharmaceutical preparation thereof during about 1 to about 7 days each month.

Within the context of this invention, the beneficial effect, including but not limited to an attenuation, reduction, decrease or diminishing of the pathological development after onset of the disease, may be seen after one or more a "treatments", after an "induction treatment", after a "maintenance treatment" or during a Cladribine-free period.

"Daily dose" refers to the total dose of Cladribine orally administered to the patient each day of administration. The daily dose can be reached through a single or several administrations per day, such as for example once a day, twice a day or three times a day.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Patients suffering from MS can be defined for example as having clinically definite or laboratory-definite MS according to Schumacher or Poser criteria (Schumacher et al., 1965, Ann. NY Acad. Sci. 1965; 122:552-568; Poser et al., 1983, Ann. Neurol. 13(3): 227-31).

"Relapses" involve neurologic problems that occur over a short period, typically days but sometimes as short as hours or even minutes. These attacks most often involve motor, sensory, visual or coordination problems early in the disease. Later, bladder, bowel, sexual and cognitive problems may be shown. Sometimes the attack onset occurs over several weeks. Typical MS relapse involves a period of worsening, with development of neurological deficits, then a plateau, in which the patient is not getting any better but also not getting any worse followed by a recovery period. Recovery usually begins within a few weeks.

"Efficacy" of a treatment according to the invention can be measured based on changes in the course of disease in response to a use according to the invention. For example, treatment of MS efficacy can be measured by the frequency of relapses in RRMS and the presence or absence of new lesions in the CNS as detected using methods such as MRI technique (Miller et al., 1996, Neurology, 47(Suppl 4): S217; Evans et al., 1997, Ann. Neurology, 41:125-132).

The observation of the reduction and/or suppression of MRI $T_1$ gadolinium-enhanced lesions (thought to represent areas of active inflammation) gives a primary efficacy variable.

Secondary efficacy variables include MRI $T_1$ enhanced brain lesion volume, MRI $T_1$ enhanced lesion number, MRI $T_2$ lesion volume (thought to represent total disease burden, i.e. demyelination, gliosis, inflammation and axon loss), MRI $T_1$ enhanced hypointense lesion volume (thought to represent primarily demyelination and axon loss), time-to-progression of MS, frequency and severity of exacerbations and time-to-exacerbation, Expanded Disability Status Scale score and Scripps Neurologic Rating Scale (SNRS) score (Sipe et al., 1984, Neurology, 34, 1368-1372). Methods of early and accurate diagnosis of multiple sclerosis and of following the disease progression are described in Mattson, 2002, Expert Rev. Neurotherapeutics, 319-328.

Degree of disability of MS patients can be for example measured by Kurtzke Expanded Disability Status Scale (EDSS) score (Kurtzke, 1983, Neurology, 33, 1444-1452). Typically a decrease in EDSS score corresponds to an improvement in the disease and conversely, an increase in EDSS score corresponds to a worsening of the disease.

Cladribine (2-CdA)

2-CdA and its pharmacologically acceptable salts may be used in the practice of this invention.

Cladribine can be formulated in any pharmaceutical preparation suitable for oral administration. Representative oral formulations of 2-CdA are described in (WO 96/19230; WO 96/19229; U.S. Pat. No. 6,194,395; U.S. Pat. No. 5,506,214; WO 2004/087100; WO 2004/087101), the contents of which are incorporated herein by reference. Examples of ingredients for oral formulations are given below.

Processes for preparing 2-CdA are well known in the art. For example, the preparation of 2-CdA is described in (EP 173,059; WO 04/028462; WO 04/028462; U.S. Pat. No. 5,208,327; WO 00/64918) and Robins et al., J. Am. Chem. Soc., 1984, 106: 6379. Alternatively, pharmaceutical preparations of 2-CdA may be purchased from Bedford Laboratories, Bedford, Ohio.

Oral administration of Cladribine may be in capsule, tablet, oral suspension, or syrup form. The tablet or capsules may contain from about 3 to 500 mg of Cladribine. Preferably they may contain about 3 to about 10 mg of Cladribine, more preferably about 3, about 5 or about 10 mg of Cladribine. The capsules may be gelatin capsules and may contain, in addition to Cladribine in the quantity indicated above, a small quantity, for example less than 5% by weight, magnesium stearate or other excipient. Tablets may contain the foregoing amount of the compound and a binder, which may be a gelatin solution, a starch paste in water, polyvinyl polyvinyl alcohol in water, etc. with a typical sugar coating.

In a preferred embodiment of the present invention, Cladribine is formulated in tablets. Preferably said tablets contain 3 mg or 10 mg of 2-CdA. Even more preferably said tablets are the one disclosed in table 2 here below (3 mg or 10 mg 2-CdA per tablet).

Compositions of Cladribine

Compositions of this invention may further comprise one or more pharmaceutically acceptable additional ingredient(s) such as alum, stabilizers, antimicrobial agents, buffers, coloring agents, flavoring agents, adjuvants, and the like.

Compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate). Tablets may be coated according to methods well known in the art.

Compositions of this invention may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agent include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Interferon-beta (IFN-beta or IFN-b),

According to the present invention, Cladribine is administered in combination with a therapeutically effective amount of IFN-beta. IFN-beta is administered prior to, simultaneously or sequentially with Cladribine. Active agents that are administered simultaneously with other therapeutic agents can be administered in the same or different compositions and in the same or different routes of administration.

The term "interferon-beta" (IFN-beta or IFN-b), as used in the present invention, is intended to include human fibroblast interferon, which may be native, i.e. purified from a natural source, or obtained by DNA recombinant techniques from prokaryotic sources (e.g. *Escherichia coli, E. coli*) or from eukaryotic host cells, e.g. from yeast or mammalian cells. Mammalian cells such as Chinese hamster ovary cells (CHO) or human cells are a preferred host for production of recombinant IFN-beta. The IFN-beta may be glycosylated or non-glycosylated. If IFN-beta, used in accordance with the present invention, is non-glycosylated (e.g. produced in *E. coli*), it is preferred to administer higher amounts of IFN-beta in order to obtain a biological or pharmacological effect comparable to that of glycosylated IFN-beta. For instance, an amount of non-glycosylated IFN-beta that is about 10 times higher than the amount of glycosylated IFN-beta is preferably administered in order to obtain comparable activities.

The term "interferon-beta", as used herein, also encompasses functional derivatives, muteins, analogs, and fragments, or fusion proteins of IFN-beta. Thus, the terms "interferon (IFN)" and "interferon-beta (IFN-beta)", as used herein, are intended to include fibroblast interferon in particular of human origin, as obtained by isolation from biological fluids or as obtained by DNA recombinant techniques from prokaryotic or eukaryotic host cells, as well as its salts, functional derivatives, variants, analogs and active fragments. The use of interferon of human origin is preferred in accordance with the present invention.

In one embodiment of the present invention the interferon-beta protein used is interferon-beta 1a, such as for example Avonex® (Biogen) or Rebif® (Serono). In another embodiment of the present invention the interferon-beta protein is interferon-beta 1b, such as for example Betaseron® (Berlex/Schering AG).

Preferably, the IFN-beta to be used in the frame of the present invention is Betaseron® (Berlex/Schering AG); Avonex® (Biogen); or Rebif® (Serono). Even preferred IFN-beta, is Rebif® (Serono).

Rebif® (interferon beta-1a) is a purified 166 amino acid glycoprotein with a molecular weight of approximately 22,500 daltons. It is produced by recombinant DNA technology using genetically engineered Chinese Hamster Ovary cells into which the human interferon beta gene has been introduced. The amino acid sequence of Rebif® is identical to that of natural fibroblast derived human interferon beta. Natural interferon beta and interferon beta-1a (Rebif®) are glycosylated with each containing a single N-linked complex carbohydrate moiety.

Using a reference standard calibrated against the World Health Organization natural interferon beta standard (Second International Standard for Interferon, Human Fibroblast GB 23 902 531), Rebif® has a specific activity of approximately 270 million international units (MIU) of antiviral activity per mg of interferon beta-1a determined in an in vitro cytopathic effect bioassay using WISH cells and Vesicular Stomatitis virus.

| Conversion table for MIU and mcg of IFN-beta | | | | |
|---|---|---|---|---|
| MIU | 3 | 12 | 18 | 24 |
| mcg | 11 | 44 | 66 | 88 |

Rebif ® 44 mcg contains approximately 12 MIU of antiviral activity using this method.

Rebif® (recombinant human interferon-beta) is the latest development in interferon therapy for multiple sclerosis (MS) and represents a significant advance in treatment. Rebif® is interferon (IFN)-beta 1a, produced from mammalian cell lines. It was established that interferon beta-1a given subcutaneously three times per week is efficacious in the treatment of Relapsing-Remitting Multiple Sclerosis (RRMS). Interferon beta-1a can have a positive effect on the long-term course of MS by reducing number and severity of relapses and reducing the burden of the disease and disease activity as measured by MRI.

In accordance with the present invention, where IFN-beta is recombinant IFN-beta 1b produced in *E. Coli*, commercially available under the trademark Betaseron, it may preferably be administered sub-cutaneously every second day at a dosage of about of 250 to 300 mcg or 8 MIU to 9.6 MIU per person.

In accordance with the present invention, where IFN-beta is recombinant IFN-beta 1a, produced in Chinese Hamster Ovary cells (CHO cells), commercially available under the trademark Avonex, it may preferably be administered intramuscularly once a week at a dosage of about of 30 mcg to 33 mcg or 6 MIU to 6.6 MIU per person.

In accordance with the present invention, when IFN-beta is recombinant IFN-beta 1a, produced in Chinese Hamster Ovary cells (CHO cells), commercially available under the trademark Rebif, it may preferably be administered sub-cutaneously three times a week (TIW) at a dosage of 22 to 44 mcg or 6 MIU to 12 MIU per person. Preferably, a dosage of 44 mcg or 12 MIU per application is chosen.

IFN-beta proteins according to the present invention may include functional derivatives, variants and muteins of IFN-beta.

"Functional derivatives" as used herein cover derivatives of IFN-beta, and its variants or muteins and fused proteins, which may be prepared from the functional groups which occur as side chains on the residues or the N or C terminal groups, by means known in the art.

These functional derivatives are included in the invention as long as they remain pharmaceutically acceptable, i.e. they do not destroy the activity of the protein, which is substantially similar to, or better than, the activity of IFN-beta, and do not confer toxic properties on compositions containing it.

These derivatives may, for example, include polyethylene glycol side chains, which may improve other properties of the protein, such as the stability, half-life, bioavailability, tolerance by the human body, or immunogenicity. To achieve this goal, IFN-beta may be linked e.g. to Polyethlyenglycol (PEG). PEGylation may be carried out by known methods, described in WO 92/13095, for example. In particular, PEG-IFN can be prepared in accordance with the teaching of WO 99/55377.

Therefore, in a preferred embodiment, the functional derivative of IFN-beta comprises at least one moiety attached to one or more functional groups, which occur as one or more side chains on the amino acid residues. An embodiment in which the moiety is a polyethylene glycol (PEG) moiety is highly preferred. In accordance with the present invention, several PEG moieties may also be attached to the IFN-beta.

Other derivatives include a modified interferon-beta protein, such as a long-acting form interferon-beta. In particular, the long-acting interferon-beta may be selected from pegylated interferon-beta, interferon-beta-HAS fusion proteins, and interferon-beta-Fc-fusion proteins.

Other derivatives include aliphatic esters of the carboxyl groups, amides of the carboxyl groups by reaction with ammonia or with primary or secondary amines, N acyl derivatives of free amino groups of the amino acid residues formed with acyl moieties (e.g. alkanoyl or carbocyclic aroyl groups) or O acyl derivatives of free hydroxyl groups (for example that of seryl or threonyl residues) formed with acyl moieties.

"Variants" or "muteins", as used in the fame of the present invention, refer to analogs of IFN-beta, in which one or more of the amino acid residues of natural IFN-beta are replaced by different amino acid residues, or are deleted, or one or more amino acid residues are added to the natural sequence IFN-beta, without diminishing considerably the activity of the resulting products as compared with the wild type IFN-beta. These muteins are prepared by known synthesis and/or by site-directed mutagenesis techniques, or any other known technique suitable therefor.

The "variant" or "mutein" in accordance with the present invention include proteins encoded by a nucleic acid, such as DNA or RNA, which hybridizes to DNA or RNA encoding IFN-beta as disclosed e.g. in U.S. Pat. No. 4,738,931 under stringent conditions. The term "stringent conditions" refers to hybridization and subsequent washing conditions, which those of ordinary skill in the art conventionally refer to as "stringent". See Ausubel et al., Current Protocols in Molecular Biology, Interscience, N.Y., §§6.3 and 6.4 (1987, 1992). Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30 60 minutes and then, a 0.1×SSC and 0.5% SDS at 68° C. for 30 60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al., 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at See Worldwide Website ncbi.nlm.nih.gov) and FASTA (Pearson W R, 1990).

The "variant" or "mutein" in accordance with the present invention include proteins having a sequence of amino acids sufficiently duplicative of that of IFN-beta, such as to have substantially similar activity to IFN-beta. A functional assay for evaluating whether any variant or mutein has a similar activity as IFN-beta is e.g. the assay measuring the activity of interferon on the cytopathic effect of vesicular stomatitis virus in WISH cells, e.g. described by Youcefi et al., 1985. Thus, it can be determined whether any given mutein has substantially the same activity as IFN-beta by means of routine experimentation.

In a preferred embodiment, any such variant or mutein has at least 40% identity or homology with the sequence of IFN-beta as disclosed e.g. in U.S. Pat. No. 4,738,931. More preferably, it has at least 50%, at least 60%, at least 70%, at least 80% or, most preferably, at least 90% identity or homology thereto.

Muteins of IFN-beta, which can be used in accordance with the present invention, or nucleic acid coding thereof, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of IFN-beta polypeptides may include synonymous amino acids within a group which have sufficiently similar physico-chemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |

TABLE II-continued

More Preferred Groups of Synonymous Amino Acids

| Amino Acid | Synonymous Group |
|---|---|
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IFN-beta for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

The "variant" or "mutein" in accordance with the present invention include also the so-called "consensus interferons". "Consensus interferons" are non-naturally occurring variants of IFN (U.S. Pat. No. 6,013,253). Consensus interferons may also be used according to the invention.

In accordance with the present invention, a salt of IFN-beta may also be used for treatment of Multiple Sclerosis.

The term "salts" herein refers to both salts of carboxyl groups and to acid addition salts of amino groups of the proteins described above or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of IFN-beta, which may be measured e.g. in the bioassay described above.

The term "fused protein" refers to a polypeptide comprising IFN-beta, or a variant or mutein or fragment thereof, fused with another protein, which, e.g., has an extended residence time in body fluids. IFN-beta may thus be fused to another protein, polypeptide or the like, e.g., an immunoglobulin or a fragment thereof.

Therefore, in a further embodiment, IFN-beta comprises an immunoglobulin fusion, i.e. IFN-beta is a fused protein comprising all or part of IFN-beta fused to all or a portion of an immunoglobulin. Methods for making immunoglobulin fusion proteins are well known in the art, such as the ones described in WO 01/03737, for example. The person skilled in the art will understand that the resulting fusion protein of the invention retains the biological activity of IFN-beta. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met (SEQ ID NO:1), or a Gly-Ser rich linker introduced between the IFN-beta sequence and the sequence derived from an immunoglobulin sequence. The resulting fusion protein has improved properties, such as an extended residence time in body fluids (half-life), increased specific activity, increased expression level, or the purification of the fusion protein is facilitated.

In a further preferred embodiment, IFN-beta is fused to the constant region of an Ig molecule, often called the Fc part of the immunoglobulin. Preferably, it is fused to heavy chain regions, like the CH2 and CH3 domains of human IgG1, for example. Other isoforms of Ig molecules are also suitable for the generation of fusion proteins according to the present invention, such as isoforms IgG2, IgG3 or IgG4, or other Ig classes, like IgM or IgA, for example. Fusion proteins may be monomeric or multimeric, hetero- or homomultimeric. Methods of preparing immunoblobulin fusion proteins are known in the art, e.g. from EP 526 452 or from U.S. Pat. No. 5,155,027. Ig fusion proteins comprising IFN-beta moieties are described e.g. in EP 227 110, U.S. Pat. No. 5,541,087, WO 97/24137 or WO 00/23472.

A "fragment" according to the present invention refers to any subset of IFN-beta, that is, a shorter peptide, which retains the desired biological activity as measurable e.g. in the bioassay described above. Fragments may readily be prepared by removing amino acids from either end of the molecule and testing the resultant for its properties as a receptor agonist. Proteases for removing one amino acid at a time from either the N-terminal or the C-terminal of a polypeptide are known, and so determining fragments, which retain the desired biological activity, may be determined e.g. in the test described by Youcefi et al., 1985, and involves only routine experimentation.

While the present invention provides recombinant methods for making the above-defined derivatives, these derivatives may also be made by conventional protein synthesis methods, which are well known to those skilled in the art.

IFN-beta, or a variant/mutein, functional derivative, active fragment or fusion protein thereof having IFN-beta activity, is preferably administered systemically, and preferably subcutaneously or intramuscularly. Intradermal, transdermal (e.g. in slow release formulations), intravenous, oral, intracranial, epidural, topical, rectal, and intranasal routes are also within the present invention.

Any other therapeutically efficacious route of administration may also be used, for example absorption through epithelial or endothelial tissues or by gene therapy wherein a DNA molecule encoding the IFN-beta is administered to the patient (e.g. via a vector), which causes IFN-beta to be expressed and secreted in vivo.

IFN-beta may be formulated as a pharmaceutical composition, i.e. together with a pharmaceutically acceptable carrier, excipients or the like. The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

In accordance with the present invention, when IFN-beta is recombinant IFN-beta 1a, produced in Chinese Hamster Ovary cells (CHO cells), commercially available under the trademark Rebif, it may preferably be formulated as HSA (Human Serum Albumin)-free formulation (containing recombinant interferon beta-1a plus excipients) as disclosed in WO2004/096263.

The dosage administered, as single or multiple doses, to an individual may vary depending upon a variety of factors, including IFN-beta pharmacokinetic properties, the route of administration, patient conditions and characteristics (sex, age, body weight, health, size), extent of symptoms, concurrent treatments, frequency of treatment. Adjustment and manipulation of established dosage ranges may be determined by those skilled in the art.

In one embodiment of the present invention the IFN-beta is dosed at least at 44 mcg subcutaneously per administration. Preferred doses and regimens in accordance with the present invention are selected from the group consisting of: 12 MIU (44 mcg) of IFN-beta three times a week, 12 MIU (44 mcg) daily, 24 MIU (88 mcg) three times a week, 24 MIU (88 mcg) daily. These doses are preferably administered subcutaneously. In one particularly preferred embodiment the IFN-beta is dosed at 44 mcg subcutaneously three times a week.

It is also preferred to administer IFN-beta at 100 mcg (about 27 MIU) once per week intramuscularly.

The daily doses may also be given in divided doses or in sustained release form effective to obtain the desired results. Second or subsequent administrations can be performed at a dosage which is the same, less than or greater than the initial or previous dose administered to the individual.

Patients

The patients to be treated according to the method of the present invention are patients suffering from multiple sclerosis, who are refractory to at least one conventional therapy for MS.

Preferably the refractory patients are treated with a conventional therapy for MS, which is not clinically adequate to relieve one or more symptoms associated with such disorder. Typically, such patients are suffering from multiple sclerosis but are experiencing worsening or stagnation of the symptoms of the disease in spite of being treated for MS with such conventional therapy and require additional therapy to ameliorate the symptoms associated with their disorder.

In an embodiment of the present invention, the conventional therapy is selected from the group consisting of: treatment with beta interferon, treatment with Glatimarer Acetate (Copaxone®, Teva), treatment with natalizumab (Tysabri®, Biogen/Elan), or treatment with Mitoxantrone (Novantrone®, Serono). In a preferred embodiment, the conventional therapy is treatment with beta interferon, preferably treatment with Betaseron® (Berlex/Schering AG); Avonex® (Biogen); or Rebif® (Serono). In an even preferred embodiment, the conventional therapy is treatment with Rebif® (Serono).

In an embodiment of the present invention, the patients to be treated according to the method of the present invention are refractory to one, two, three or four of the conventional therapies described herein.

In a particular embodiment, the refractory patients to be treated have experienced at least one relapse, in particular one, two, three, four or five relapse, irrespective of disability progression, in spite of receiving at least one conventional therapy. Preferably, the at least one relapse, in particular one, two, three, four or five relapse, occurred during the year prior the beginning of the treatment according to the present invention. In a particular embodiment, the patients to be treated have experienced at least one relapse, in particular one, two, three, four or five relapse, during the year preceding the beginning of the treatment of the present invention and have been treated with Rebif® (Serono), in particular 12 MIU (44 mcg) of Rebif® three times a week.

In a particular embodiment, the refractory patients to be treated have experienced at least one relapse, in particular one, two, three, four or five relapse, and develop increasing disability because of progressive forms of the disease, in spite of receiving at least one conventional therapy. Degree of disability of MS patients can be for example measured by Kurtzke Expanded Disability Status Scale (EDSS) score (Kurtzke, 1983, *Neurology*, 33, 1444-1452). Typically a decrease in EDSS score corresponds to an improvement in the disease and conversely, an increase in EDSS score corresponds to a worsening of the disease. In a particular embodiment, the at least one relapse, in particular one, two, three, four or five relapse, occurred during the year prior the beginning of the treatment according to the present invention. In a particular embodiment, the patients to be treated have experienced at least one relapse, in particular one, two, three, four or five relapse, during the year preceding the beginning of the treatment of the present invention and have been treated with Rebif® (Serono), in particular 12 MIU (44 mcg) of Rebif® three times a week.

In a particular embodiment, the refractory patients to be treated develop increasing disability because of progressive forms of the disease, in spite of receiving at least one conventional therapy. Degree of disability of MS patients can be for example measured by Kurtzke Expanded Disability Status Scale (EDSS) score (Kurtzke, 1983, *Neurology*, 33, 1444-1452). Typically a decrease in EDSS score corresponds to an improvement in the disease and conversely, an increase in EDSS score corresponds to a worsening of the disease. In a particular embodiment, the patients to be treated experienced an increase in their EDSS score of 0.5, 1, 1.5, 2, 2.5, 3, 3.5, 4, 4.5, 5, 5.5, 6, 6.5, 7, 7.5, 8 or 8.5, in spite of receiving at least one conventional therapy. Preferably, the increase in EDSS score is of 0.5, 1, 1.5, 2, 2.5, 3, 3.5, 4, 4.5 or 5 in spite of receiving at least one conventional therapy. Even more preferably, the increase in EDSS score is of 0.5, 1, 1.5 or 2, 2.5 in spite of receiving at least one conventional therapy. Most preferably, the increase in EDSS score is of 0.5, 1 or 1.5 (preferably 1) in spite of receiving at least one conventional therapy. In a preferred embodiment said increase in EDSS score occurred during one, two, three, four, five, six, seven, eight or ten years prior the beginning of the treatment according to the present invention. Preferably the increase in EDSS score occurred during one, two, three, four or five, years prior the beginning of the treatment according to the present invention. Even more preferably, the increase in EDSS score occurred during one, two or three years prior the beginning of the treatment according to the present invention. Most preferably, the increase in EDSS score occurred during one or two, preferably one, year prior the beginning of the treatment according to the present invention. In a preferred embodiment of the present invention, the patients to be treated experienced increase in their EDSS score associated to at least one relapse, in particular one, two, three, four, five, six, seven or ten relapses, preferably one, two, three, four or five relapses, even more preferably one, two, or three relapses, most preferably one or two (preferably one) relapses. In a particular embodiment, the patients to be treated have experienced increase in their EDSS score as disclosed here above in spite of being treated with Rebif® (Serono), in particular 12 MIU (44 mcg) of Rebif® three times a week.

In a particular embodiment, the refractory patients to be treated have acquired enhanced lesion number or enhanced brain lesion volume in the CNS as detected using methods such as MRI technique (Miller et al., 1996, *Neurology*, 47(Suppl 4): S217; Evans et al., 1997, *Ann. Neurology*, 41:125-132), in spite of receiving at least one conventional therapy. In a particular embodiment, the enhanced lesion number or enhanced brain lesion volume occurred during the year prior the beginning of the treatment according to the present invention. In a particular embodiment, the patients to be treated have acquired enhanced lesion number or enhanced brain lesion volume in the CNS during the year preceding the beginning of the treatment of the present invention and have been treated with Rebif® (Serono), in particular 12 MIU (44 mcg) of Rebif® three times a week.

In an embodiment of the present invention, the refractory patients to be treated are suffering from worsening MS, in particular secondary progressive, progressive remitting or worsening relapsing-remitting MS, in spite of being treated by conventional therapy.

In an embodiment of the present invention, refractory patients to be treated according to the method of the present invention are patients suffering from progressive relapsing multiple sclerosis (PRMS) or primary progressive multiple sclerosis (PPMS).

In an embodiment of the invention, patients are selected from human males or females between 18 and 55 years age.

Combination Therapy of Oral Cladribine and Interferon-beta (IFN-beta or IFN-b) According to the Present Invention According to the present invention, Cladribine is administered in combination with a therapeutically effective amount of IFN-beta. IFN-beta is administered prior to, simultaneously and/or sequentially with Cladribine. Active agents that are administered simultaneously with other therapeutic agents can be administered in the same or different compositions and in the same or different routes of administration.

An object of the present invention resides in the use of a combination of Cladribine and IFN-beta for the manufacture of a medicament for treating patients suffering from multiple sclerosis and who are refractory to at least one conventional therapy for multiple sclerosis, wherein Cladribine is to be orally administered following the sequential steps below:
(i) An induction period wherein Cladribine is administered and wherein the total dose of Cladribine reached at the end of the induction period is from about 1.7 mg/kg to about 3.5 mg/kg;
(ii) A Cladribine-free period wherein no Cladribine is administered;
(iii) A maintenance period wherein Cladribine is administered and wherein the total dose of Cladribine administered during the maintenance period is lower than or equal to the total dose of Cladribine reached at the end of the induction period (i);

(iv) A Cladribine-free period wherein no Cladribine is administered.

In a further embodiment, the invention provides the use of a combination of Cladribine and IFN-beta, as disclosed herein, wherein the induction period lasts up to about 4 months or up to about 3 months or up to about 2 months.

In a further embodiment, the invention provides the use of a combination of Cladribine and IFN-beta, as disclosed herein, wherein the induction period lasts up to about 2 months.

In a further embodiment, the invention provides the use of a combination of Cladribine and IFN-beta, as disclosed herein, wherein the induction period lasts up to about 4 months.

In a preferred further embodiment, the invention provides the use of a combination of Cladribine and IFN-beta, as disclosed herein, wherein the total dose of Cladribine reached at the end of the induction period is about 1.7 mg/kg, preferably 1.75 mg/kg. In a preferred embodiment, the total dose of Cladribine reached at the end of the induction period is about 1.7 mg/kg, preferably 1.75 mg/kg, and the induction period lasts up to about 2 months.

In a further preferred embodiment, the invention provides the use of a combination of Cladribine and IFN-beta, as disclosed herein, wherein the total dose of Cladribine reached at the end of the induction period is about 3.5 mg/kg, preferably 3.5 mg/kg. In a preferred embodiment, the total dose of Cladribine reached at the end of the induction period is about 3.5 mg/kg, preferably 3.5 mg/kg, and the induction period lasts up to about 4 months.

In a further embodiment, the invention provides the use of a combination of Cladribine and IFN-beta, as disclosed herein, wherein the Cladribine-free period (ii) lasts up to about 10 months, or up to about 9 months or up to about 8 months.

In a further embodiment, the invention provides the use of a combination of Cladribine and IFN-beta, as disclosed herein, wherein the Cladribine-free (ii) period lasts up to about 8 months.

In a further embodiment, the invention provides the use of a combination of Cladribine and IFN-beta, as disclosed herein, wherein the Cladribine-free (ii) period lasts at least about 8 months.

In a further embodiment, the invention provides the use of a combination of Cladribine and IFN-beta, as disclosed herein, wherein the Cladribine-free period (ii) lasts up to about 10 months.

In a further embodiment, the invention provides the use of a combination of Cladribine and IFN-beta, as disclosed herein, wherein the combined duration of the induction period (i) with the Cladribine-free period (ii) is about 1 year (about 12 months). Preferably the duration of the induction period is about 4 months and the duration of the Cladribine-free period (ii) is about 8 months, or the duration of the induction period is about 3 months and the duration of the Cladribine-free period (ii) is about 9 months, or the duration of the induction period is about 2 months and the duration of the Cladribine-free period (ii) is about 10 months.

In a further embodiment, the invention provides the use of a combination of Cladribine and IFN-beta, as disclosed herein, wherein the combined duration of the induction period (i) with the Cladribine-free period (ii) is about 1 year (about 12 months) and the total dose of Cladribine reached at the end of this year of treatment is about 1.7 mg/kg, preferably 1.75 mg/kg or about 3.5 mg/kg, preferably 3.5 mg/kg. Preferably the duration of the induction period is about 4 months and the duration of the Cladribine-free period (ii) is about 8 months, or the duration of the induction period is about 3 months and the duration of the Cladribine-free period (ii) is about 9 months, or the duration of the induction period is about 2 months and the duration of the Cladribine-free period (ii) is about 10 months.

In a further embodiment, the invention provides the use of a combination of Cladribine and IFN-beta, as disclosed herein, wherein the Cladribine-free period (iv) lasts up to about 10 months, or up to about 9 months or up to about 8 months.

In a further embodiment, the invention provides the use of a combination of Cladribine and IFN-beta, as disclosed herein, wherein the Cladribine-free (iv) period lasts up to about 10 months.

In a further embodiment, the invention provides the use of a combination of Cladribine and IFN-beta, as disclosed herein, wherein the Cladribine-free (iv) period lasts at least about 8 months.

In a further embodiment, the invention provides the use of a combination of Cladribine and IFN-beta, as disclosed herein, wherein the Cladribine-free periods (ii) and/or (iv) last between about 8 and about 10 months.

In a further embodiment, the invention provides the use of a combination of Cladribine and IFN-beta, as disclosed herein, wherein a placebo-pill is administered during the Cladribine-free period.

In a further embodiment, the invention provides the use of a combination of Cladribine and IFN-beta, as disclosed herein, wherein the Cladribine-free period is free of any administration.

In a further embodiment, the invention provides the use of a combination of Cladribine and IFN-beta, as disclosed herein, wherein the maintenance period lasts up to about 4 months, or up to about 3 months, or up to about 2 months, preferably up to about 2 months.

In a further embodiment, the invention provides the use of a combination of Cladribine and IFN-beta, as disclosed herein, wherein the total dose of Cladribine administered during the maintenance period (iii) is about 1.7 mg/kg, preferably 1.75 mg/kg. In a further preferred embodiment, the total dose of Cladribine administered during the maintenance period is about 1.7 mg/kg, preferably 1.75 mg/kg, and the maintenance period lasts up to about 2 months.

In a further embodiment, the invention provides the use of a combination of Cladribine and IFN-beta, as disclosed herein, wherein the combined duration of the maintenance period (iii) with the Cladribine-free period (iv) is about 1 year (about 12 months). Preferably the duration of the maintenance period (iii) is about 4 months and the duration of the Cladribine-free period (iv) is about 8 months, or the duration of the maintenance period (iii) is about 3 months and the duration of the Cladribine-free period (iv) is about 9 months. Even more preferably, the duration of the maintenance period (iii) is about 2 months and the duration of the Cladribine-free period (iv) is about 10 months.

In a further embodiment, the invention provides the use of a combination of Cladribine and IFN-beta, as disclosed herein, wherein the combined duration of the maintenance period (iii) with the Cladribine-free period (iv) is about 1 year (about 12 months) and the total dose of Cladribine administered during this year of treatment is about 1.7 mg/kg, preferably 1.75 mg/kg. Preferably the duration of the maintenance period (iii) is about 4 months and the duration of the Cladribine-free period (iv) is about 8 months, or the duration of the maintenance period (iii) is about 3 months and the duration of the Cladribine-free period (iv) is about 9 months. Even more preferably, the duration of the maintenance period (iii) is about 2 months and the duration of the Cladribine-free period (iv) is about 10 months.

In a further embodiment, the invention provides the use of a combination of Cladribine and IFN-beta, as disclosed herein, wherein the combined duration of the induction period (i), the Cladribine-free period (ii), the maintenance period (iii) and the Cladribine-free period (iv) is about 2 years (about 24 months). In an embodiment, the duration of the induction period is about 4 months, the duration of the Cladribine-free period (ii) is about 8 months, the duration of the maintenance period (iii) is about 4 months and the duration of the Cladribine-free period (iv) is about 8 months. In another embodiment, the duration of the induction period is about 4 months, the duration of the Cladribine-free period (ii) is about 8 months, the duration of the maintenance period (iii) is about 3 months and the duration of the Cladribine-free period (iv) is about 9 months. In another embodiment, the duration of the induction period is about 4 months, the duration of the Cladribine-free period (ii) is about 8 months, the duration of the maintenance period (iii) is about 2 months and the duration of the Cladribine-free period (iv) is about 10 months. In another embodiment, the duration of the induction period is about 3 months, the duration of the Cladribine-free period (ii) is about 9 months, the duration of the maintenance period (iii) is about 4 months and the duration of the Cladribine-free period (iv) is about 8 months. In another embodiment, the duration of the induction period is about 3 months, the duration of the Cladribine-free period (ii) is about 9 months, the duration of the maintenance period (iii) is about 3 months and the duration of the Cladribine-free period (iv) is about 9 months. In another embodiment, the duration of the induction period is about 3 months, the duration of the Cladribine-free period (ii) is about 9 months, the duration of the maintenance period (iii) is about 2 months and the duration of the Cladribine-free period (iv) is about 10 months. In another embodiment, the duration of the induction period is about 2 months, the duration of the Cladribine-free period (ii) is about 10 months, the duration of the maintenance period (iii) is about 4 months and the duration of the Cladribine-free period (iv) is about 8 months. In another embodiment, the duration of the induction period is about 2 months, the duration of the Cladribine-free period (ii) is about 10 months, the duration of the maintenance period (iii) is about 3 months and the duration of the Cladribine-free period (iv) is about 9 months. In another embodiment, the duration of the induction period is about 2 months, the duration of the Cladribine-free period (ii) is about 10 months, the duration of the maintenance period (iii) is about 2 months and the duration of the Cladribine-free period (iv) is about 10 months.

In a further embodiment, the invention provides the use of a combination of Cladribine and IFN-beta, as disclosed herein, wherein the combined duration of the induction period (i) and the Cladribine-free period (ii) is about 1 year (12 months), the combined duration of the maintenance period (iii) and the Cladribine-free period (iv) is about 1 year (about 12 months), the total dose of Cladribine administered during the first year of treatment is about 1.7 mg/kg, preferably 1.75 mg/kg and the total dose of Cladribine administered during the second year of treatment is about 1.7 mg/kg, preferably 1.75 mg/kg. In an embodiment, the duration of the induction period is about 4 months, the duration of the Cladribine-free period (ii) is about 8 months, the duration of the maintenance period (iii) is about 4 months and the duration of the Cladribine-free period (iv) is about 8 months. In another embodiment, the duration of the induction period is about 4 months, the duration of the Cladribine-free period (ii) is about 8 months, the duration of the maintenance period (iii) is about 3 months and the duration of the Cladribine-free period (iv) is about 9 months. In another embodiment, the duration of the induction period is about 4 months, the duration of the Cladribine-free period (ii) is about 8 months, the duration of the maintenance period (iii) is about 2 months and the duration of the Cladribine-free period (iv) is about 10 months. In another embodiment, the duration of the induction period is about 3 months, the duration of the Cladribine-free period (ii) is about 9 months, the duration of the maintenance period (iii) is about 4 months and the duration of the Cladribine-free period (iv) is about 8 months. In another embodiment, the duration of the induction period is about 3 months, the duration of the Cladribine-free period (ii) is about 9 months, the duration of the maintenance period (iii) is about 3 months and the duration of the Cladribine-free period (iv) is about 9 months. In another embodiment, the duration of the induction period is about 3 months, the duration of the Cladribine-free period (ii) is about 9 months, the duration of the maintenance period (iii) is about 2 months and the duration of the Cladribine-free period (iv) is about 10 months. In another embodiment, the duration of the induction period is about 2 months, the duration of the Cladribine-free period (ii) is about 10 months, the duration of the maintenance period (iii) is about 4 months and the duration of the Cladribine-free period (iv) is about 8 months. In another embodiment, the duration of the induction period is about 2 months, the duration of the Cladribine-free period (ii) is about 10 months, the duration of the maintenance period (iii) is about 3 months and the duration of the Cladribine-free period (iv) is about 9 months. In another embodiment, the duration of the induction period is about 2 months, the duration of the Cladribine-free period (ii) is about 10 months, the duration of the maintenance period (iii) is about 2 months and the duration of the Cladribine-free period (iv) is about 10 months.

In a further embodiment, the invention provides the use of a combination of Cladribine and IFN-beta, as disclosed herein, wherein the combined duration of the induction period (i) and the Cladribine-free period (ii) is about 1 year (12 months), the combined duration of the maintenance period (iii) and the Cladribine-free period (iv) is about 1 year (about 12 months), the total dose of Cladribine administered during the first year of treatment is about 3.5 mg/kg, preferably 3.5 mg/kg and the total dose of Cladribine administered during the second year of treatment is about 1.7 mg/kg, preferably 1.75 mg/kg. In an embodiment, the duration of the induction period is about 4 months, the duration of the Cladribine-free period (ii) is about 8 months, the duration of the maintenance period (iii) is about 4 months and the duration of the Cladribine-free period (iv) is about 8 months. In another embodiment, the duration of the induction period is about 4 months, the duration of the Cladribine-free period (ii) is about 8 months, the duration of the maintenance period (iii) is about 3 months and the duration of the Cladribine-free period (iv) is about 9 months. In another embodiment, the duration of the induction period is about 4 months, the duration of the Cladribine-free period (ii) is about 8 months, the duration of the maintenance period (iii) is about 2 months and the duration of the Cladribine-free period (iv) is about 10 months. In another embodiment, the duration of the induction period is about 3 months, the duration of the Cladribine-free period (ii) is about 9 months, the duration of the maintenance period (iii) is about 4 months and the duration of the Cladribine-free period (iv) is about 8 months. In another embodiment, the duration of the induction period is about 3 months, the duration of the Cladribine-free period (ii) is about 9 months, the duration of the maintenance period (iii) is about 3 months and the duration of the Cladribine-free period (iv) is about 9 months. In another embodiment, the duration of the induction period is about 3 months, the duration of the Cladribine-free period (ii) is about 9 months, the duration of the maintenance period (iii) is about 2 months and the duration of the Cladribine-free period (iv) is about 10 months. In another embodiment, the duration of the induction period is about 2 months, the duration of the Cladribine-free period (ii) is about 10 months, the duration of the maintenance period (iii) is about 4 months and the duration of the Cladribine-free period (iv) is about 8 months. In another embodiment, the duration of the induction period is about 2 months, the duration of the Cladribine-free period (ii) is about 10 months, the duration of the maintenance period (iii) is about 3 months and the duration of the Cladribine-free period (iv) is about 9 months. In another embodiment, the duration of the induction period is about 2 months, the duration of the Cladribine-free period (ii) is about 10 months, the duration of the maintenance period (iii) is about 2 months and the duration of the Cladribine-free period (iv) is about 10 months.

In a further embodiment, the invention provides the use of a combination of Cladribine and IFN-beta, as disclosed herein, wherein the steps (iii) to (iv) are repeated at least one, two or three times.

Another preferred embodiment of the present invention resides in the use of a combination of Cladribine IFN-beta for the manufacture of a medicament for treating patients suffering from multiple sclerosis and who are refractory to at least one conventional therapy for multiple sclerosis, wherein Cladribine is to be orally administered following the sequential steps below:
  (i) An induction period wherein Cladribine is administered and wherein the total dose of Cladribine reached at the end of the induction period is from about 1.7 mg/kg to about 3.5 mg/kg;
  (ii) A Cladribine-free period wherein no Cladribine is administered;
  (iii) A maintenance period wherein Cladribine is administered and wherein the total dose of Cladribine administered during the maintenance period is lower than or equal to the total dose of Cladribine reached at the end of the induction period (i)
  (iv) A Cladribine-free period wherein no Cladribine is administered;
wherein the induction period last up to about 4 months, or up to about 3 months, or up to about 2 months; the Cladribine-free period (ii) lasts up to about 10 months, or up to about 9 months, or up to about 8 months; the maintenance period (iii) lasts up to about 2 months; the Cladribine-free period (iv) lasts up to about 10 months; the total dose of Cladribine administered during the maintenance period is about 1.7 mg/kg and steps (iii) to (iv) are performed one, two or three times.

In another embodiment, the invention provides the use of a combination of Cladribine and IFN-beta for the manufacture of a medicament for treating patients suffering from multiple sclerosis and who are refractory to at least one conventional therapy for multiple sclerosis, wherein Cladribine is to be orally administered following the sequential steps below:
  (i) An induction period wherein Cladribine is administered and wherein the total effective dose of Cladribine reached at the end of the induction period is from about 0.7 mg/kg to about 1.4 mg/kg;
  (ii) A Cladribine-free period wherein no Cladribine is administered;
  (iii) A maintenance period wherein Cladribine is administered and wherein the total effective dose of Cladribine administered during the maintenance period (iii) is lower than or equal to the total effective dose of Cladribine reached at the end of the induction period (i);
  (iv) A Cladribine-free period wherein no Cladribine is administered.

In a further embodiment, the invention provides the use of a combination of Cladribine and IFN-beta for the manufacture of a medicament for treating patients suffering from multiple sclerosis and who are refractory to at least one conventional therapy for multiple sclerosis, wherein Cladribine is to be orally administered following the sequential steps below:
  (i) An induction period wherein Cladribine is administered and wherein the total effective dose of Cladribine reached at the end of the induction period is from about 0.7 mg/kg to about 1.4 mg/kg;
  (ii) A Cladribine-free period wherein no Cladribine is administered;
  (iii) A maintenance period wherein Cladribine is administered and wherein the total effective dose of Cladribine administered during the maintenance period is lower than the total effective dose of Cladribine reached at the end of the induction period (i);
  (iv) A Cladribine-free period wherein no Cladribine is administered;
wherein the induction period lasts up to about 4 months, or up to about 3 months, or up to about 2 months; the Cladribine-free period (ii) lasts up to about 10 months, or up to about 9 months, or up to about 8 months; the maintenance period (iii) lasts up to about 2 months; the Cladribine-free period (ii) lasts up to about 10 months; the total effective dose of Cladribine administered during the maintenance period is about 0.7 mg/kg and steps (iii) to (iv) are performed one, two or three times.

In another preferred embodiment, the invention provides the use of a combination of Cladribine and IFN-beta for the manufacture of a medicament for treating patients suffering from multiple sclerosis and who are refractory to at least one conventional therapy for multiple sclerosis, wherein Cladribine is to be orally administered following the sequential steps below:
  (i) An induction period wherein Cladribine is administered and wherein the total dose of Cladribine reached at the end of the induction period is from about 1.7 mg/kg to about 3.5 mg/kg;
  (ii) A Cladribine-free period wherein no Cladribine is administered;
  (iii) A maintenance period wherein Cladribine is administered and wherein the total dose of Cladribine administered during the maintenance period is lower than the total dose of Cladribine reached at the end of the induction period (i);
  (iv) A Cladribine-free period wherein no Cladribine is administered;
wherein the induction period last up to about 4 months, or up to about 3 months, or up to about 2 months; the Cladribine-free period (ii) lasts up to about 10 months, or up to about 9 months, or up to about 8 months; the maintenance period (iii) lasts up to about 2 months; the Cladribine-free period (iv) lasts up to about 10 months; the total dose of Cladribine administered during the maintenance period is about 1.7 mg/kg and steps (iii) to (iv) are performed one, two or three times.

In a further embodiment, the invention provides the use of a combination of Cladribine and IFN-beta, as disclosed herein, wherein Cladribine is to be orally administered at a daily dose of about 3 to 30 mg Cladribine, preferably 5 to 20 mg Cladribine, most preferably 10 mg Cladribine.

In a further embodiment, the invention provides the use of a combination of Cladribine and IFN-beta, as disclosed herein, wherein the total dose of Cladribine reached at the end of the induction period is about 3.5 mg/kg and the total dose of Cladribine administered during the maintenance period is about 1.7 mg/kg, preferably 1.75 mg/kg.

In a further embodiment, the invention provides the use of a combination of Cladribine and IFN-beta, as disclosed herein, wherein the total effective dose of Cladribine reached at the end of the induction period is about 1.4 mg/kg and the total effective dose of Cladribine administered during the maintenance period is about 0.7 mg/kg.

In a further embodiment, the invention provides the use of a combination of Cladribine and IFN-beta, as disclosed herein, wherein Cladribine is to be orally administered once a day during the induction period.

In a further embodiment, the invention provides the use of a combination of Cladribine and IFN-beta, as disclosed herein, wherein Cladribine is to be orally administered several times a day during the induction period, preferably twice or three times a day, more preferably twice a day.

In a further embodiment, the invention provides the use of a combination of Cladribine and IFN-beta, as disclosed herein, whereby Cladribine is orally administered about 1 to about 7 days per month, preferably from about 4 to about 7 days per month during the induction period, and even preferably 4 or 5 days per month during the induction period.

In a further embodiment, the invention provides the use of a combination of Cladribine and IFN-beta, as disclosed herein, whereby Cladribine is orally administered about 0.02 days/kg to about 0.08 days/kg per month during the induction period.

In a further embodiment, the invention provides the use of a combination of Cladribine and IFN-beta, as disclosed herein, whereby Cladribine is orally administered about 0.02 days/kg to about 0.08 days/kg per month during the maintenance period.

In a further embodiment, the invention provides the use of a combination of Cladribine and IFN-beta, as disclosed herein, wherein Cladribine is to be orally administered at a daily dose of about 10 mg Cladribine from day 1 to about day 2 each month during the induction period.

In a further embodiment, the invention provides the use of a combination of Cladribine and IFN-beta, as disclosed herein, wherein Cladribine is to be orally administered at a daily dose of about 10 mg Cladribine from day 1 to about day 3 each month during the induction period.

In a further embodiment, the invention provides the use of a combination of Cladribine and IFN-beta, as disclosed herein, wherein Cladribine is to be orally administered at a daily dose of about 10 mg Cladribine from day 1 to about day 4 each month during the induction period.

In a further embodiment, the invention provides the use of a combination of Cladribine and IFN-beta, as disclosed herein, wherein Cladribine is to be orally administered at a daily dose of about 10 mg Cladribine from day 1 to about day 5 each month during the induction period.

In a further embodiment, the invention provides the use of a combination of Cladribine and IFN-beta, as disclosed herein, wherein Cladribine is to be orally administered at a daily dose of about 10 mg Cladribine from day 1 to about day 6 each month during the induction period.

In a further embodiment, the invention provides the use of a combination of Cladribine and IFN-beta, as disclosed herein, wherein Cladribine is to be orally administered in a formulation described in WO 2004/087101 or in WO 2004/087100. A formulation of Cladribine particularly preferred is the one described in WO 2004/087101, Example 3 or in table 2 of example 1 of the present application.

In a further embodiment, the invention provides the use of a combination of Cladribine and IFN-beta, as disclosed herein, wherein Cladribine is to be orally administered at a daily dose of about 10 mg Cladribine from day 1 to about day 4 each month during the induction period and wherein the pharmaceutical formulation is a pharmaceutical formulation described in WO 2004/087101 or in WO 2004/087100.

In a further embodiment, the invention provides the use of a combination of Cladribine and IFN-beta, as disclosed herein, wherein Cladribine is to be orally administered at a daily dose of about 10 mg Cladribine from day 1 to about day 5 each month during the induction period and wherein the pharmaceutical formulation is a pharmaceutical formulation described in WO 2004/087101 or in WO 2004/087100.

As disclosed here above, Cladribine is administered in combination with a therapeutically effective amount of IFN-beta. The administration of oral Cladribine and IFN-beta may be simultaneous, separate or sequential. Therefore an object of the present invention resides in any use of a combination of Cladribine and IFN-beta disclosed herein, wherein Cladribine is to be orally administered following the sequential steps disclosed herein and wherein IFN-beta is administered simultaneously, separately or sequentially with oral Cladribine.

Another object of the present invention resides in the use of a combination of Cladribine and IFN-beta as disclosed herein, wherein Cladribine is to be orally administered following the sequential steps disclosed herein and wherein IFN-beta is administered before the induction period (i), and/or after the maintenance period (iii).

Another object of the present invention resides in the use of a combination of Cladribine and IFN-beta as disclosed herein, wherein Cladribine is to be orally administered following the sequential steps disclosed herein and wherein IFN-beta is administered during the Cladribine-free period (ii) and/or (iv).

In a preferred embodiment of the present invention IFN-beta is administered simultaneously with oral Cladribine. Therefore, another object of the present invention resides in the use of a combination of Cladribine and IFN-beta as disclosed herein, wherein Cladribine is to be orally administered following the sequential steps disclosed herein and wherein IFN-beta is administered during the induction period (i) and/or the maintenance period (iv). Even more preferably, IFN-beta is administered during the induction period (i), the maintenance period (iv) and the Cladribine-free periods (ii) and (iv). Even more preferably, IFN-beta is administered before the induction period (i), during the induction period (i), during the maintenance period (iv), during the Cladribine-free periods (ii) and (iv) and after the Cladribine-free period (iv).

As disclosed here above, in a preferred embodiment of the present invention the IFN-beta protein is chosen in the group consisting of: interferon-beta 1a, such as for example Avonex® (Biogen) or Rebif® (Serono), and interferon-beta 1b, such as for example Betaseron® (Berlex/Schering AG). Preferably, the IFN-beta to be used in the frame of the present invention is Rebif® (Serono).

IFN-beta is preferably administered systemically, and preferably subcutaneously or intramuscularly. In one embodiment of the present invention the IFN-beta is dosed at least at 44 mcg subcutaneously per administration. Preferred doses and regimens in accordance with the present invention are selected from the group consisting of: 12 MIU (44 mcg) of IFN-beta three times a week, 12 MIU (44 mcg) daily, 24 MIU (88 mcg) three times a week, 24 MIU (88 mcg) daily. These doses are preferably administered subcutaneously. In one particularly preferred embodiment the IFN-beta is dosed at 44 mcg subcutaneously three times a week, preferably in this case the IFN-beta used is Rebif® (Serono).

Methods of Treatment Using a Combination Therapy of Oral Cladribine and Interferon-beta (IFN-beta or IFN-b) According to the Present Invention In another embodiment, the invention provides the use of a combination of Cladribine and IFN-beta for treating patients suffering from multiple sclerosis and who are refractory to at least one conventional therapy for multiple sclerosis, comprising the oral administration of Cladribine following the sequential steps below:
  (i) An induction period wherein Cladribine is administered and wherein the total dose of Cladribine reached at the end of the induction period is from about 1.5 mg/kg to about 3.5 mg/kg;
  (ii) A Cladribine-free period wherein no Cladribine is administered;
  (iii) A maintenance period wherein Cladribine is administered and wherein the total dose of Cladribine administered during the maintenance period is lower than or equal to the total dose of Cladribine reached at the end of the induction period (i);
  (iv) A Cladribine-free period wherein no Cladribine is administered.

In a preferred embodiment, the invention provides the use of a combination of Cladribine and IFN-beta for treating patients suffering from multiple sclerosis and who are refractory to at least one conventional therapy for multiple sclerosis, comprising the oral administration of Cladribine following the sequential steps below:
  (i) An induction period wherein Cladribine is administered and wherein the total effective dose of Cladribine reached at the end of the induction period is from about 0.7 mg/kg to about 1.4 mg/kg;
  (ii) A Cladribine-free period wherein no Cladribine is administered;
  (iii) A maintenance period wherein Cladribine is administered and wherein the total effective dose of Cladribine administered during the maintenance period is lower than or equal to the total effective dose of Cladribine reached at the end of the induction period (i);
  (iv) A Cladribine-free period wherein no Cladribine is administered.

In a further embodiment, the invention provides the use of a combination of Cladribine and IFN-beta, as disclosed herein, wherein the steps (iii) to (iv) are repeated at least one or two times.

In a preferred embodiment, the invention provides the use of a combination of Cladribine and IFN-beta for treating patients suffering from multiple sclerosis and who are refractory to at least one conventional therapy for multiple sclerosis, comprising the oral administration of Cladribine following the sequential steps below:
  (i) Administering Cladribine, such that the total dose of Cladribine reached at the end of the induction period is from about 1.7 mg/kg to about 3.5 mg/kg;
  (ii) Administering no Cladribine during a Cladribine free period;
  (iii) Administering Cladribine such that the total dose of Cladribine administered during a maintenance period is lower than or equal to the total dose of Cladribine reached at the end of the induction period (i);
  (iv) And optionally, a Cladribine-free period wherein no Cladribine is administered.

In a further embodiment, the invention provides the use of a combination of Cladribine and IFN-beta, as disclosed herein, wherein the induction period lasts up to about 4 months, or up to about 3 months, or up to about 2 months.

In a further preferred embodiment, the invention provides the use of a combination of Cladribine and IFN-beta, as disclosed herein, wherein the total dose of Cladribine reached at the end of the induction period is about 1.7 mg/kg, preferably 1.75 mg/kg. In a preferred embodiment, the total dose of Cladribine reached at the end of the induction period is about 1.7 mg/kg, preferably 1.75 mg/kg, and the induction period lasts up to about 2 months.

In a further preferred embodiment, the invention provides the use of a combination of Cladribine and IFN-beta, as disclosed herein, wherein the total dose of Cladribine reached at the end of the induction period is about 3.5 mg/kg, preferably 3.5 mg/kg. In a preferred embodiment, the total dose of Cladribine reached at the end of the induction period is about 3.5 mg/kg, preferably 3.5 mg/kg, and the induction period lasts up to about 4 months.

In a further preferred embodiment, the invention provides the use of a combination of Cladribine and IFN-beta, as disclosed herein, wherein the total effective dose of Cladribine reached at the end of the induction period is about 1.4 mg/kg.

In a further preferred embodiment, the invention provides the use of a combination of Cladribine and IFN-beta, as disclosed herein, wherein the Cladribine-free period lasts up to about 10 months, or up to about 9 months, or up to about 8 months.

In a further preferred embodiment, the invention provides the use of a combination of Cladribine and IFN-beta, as disclosed herein, wherein the maintenance period lasts up to about 4 months, or up to about 3 months or up to about 2 months.

In a further preferred embodiment, the invention provides the use of a combination of Cladribine and IFN-beta, as disclosed herein, wherein the total dose of Cladribine administered during the maintenance period is about 1.7 mg/kg, preferably 1.75 mg/kg.

In a further embodiment, the invention provides the use of a combination of Cladribine and IFN-beta, as disclosed herein, wherein the total effective dose of Cladribine administered during the maintenance period is about 0.7 mg/kg.

In a further preferred embodiment, the invention provides the use of a combination of Cladribine and IFN-beta, as disclosed herein, wherein the maintenance period is followed by a Cladribine-free period.

In a further preferred embodiment, the invention provides the use of a combination of Cladribine and IFN-beta, as disclosed herein, wherein the total dose of Cladribine reached at the end of the induction period is about 3.5 mg/kg and the total dose of Cladribine administered during the maintenance period is about 1.7 mg/kg, preferably 1.75 mg/kg.

In a further embodiment, the invention provides the use of a combination of Cladribine and IFN-beta, as disclosed herein, wherein the total effective dose of Cladribine reached at the end of the induction period is about 1.4 mg/kg and the total effective dose of Cladribine administered during the maintenance period is about 0.7 mg/kg.

In a further embodiment, the invention provides the use of a combination of Cladribine and IFN-beta, as disclosed herein, wherein Cladribine is to be orally administered at a daily dose of about 3 to about 30 mg.

In a further embodiment, the invention provides the use of a combination of Cladribine and IFN-beta, as disclosed herein, wherein Cladribine is to be orally administered at a daily dose of about 10 mg.

In a further embodiment, the invention provides the use of a combination of Cladribine and IFN-beta, as disclosed herein, wherein Cladribine is orally administered about 1 to about 7 days per month during the induction period, preferably from about 4 to about 7 days per month during the induction period, and even preferably 4 or 5 days per month during the induction period.

In a further embodiment, the invention provides the use of a combination of Cladribine and IFN-beta, as disclosed herein, wherein the steps (iii) to (iv) are repeated at least one or two times.

As disclosed here above, Cladribine is administered in combination with a therapeutically effective amount of IFN-beta. The administration of oral Cladribine and IFN-beta may be simultaneous, separate or sequential. Therefore an object of the present invention resides in any use of a combination of Cladribine and IFN-beta disclosed herein, wherein Cladribine is to be orally administered following the sequential steps disclosed herein and wherein IFN-beta is administered simultaneously, separately or sequentially with oral Cladribine.

Another object of the present invention resides in the use of a combination of Cladribine and IFN-beta as disclosed herein, wherein Cladribine is to be orally administered following the sequential steps disclosed herein and wherein IFN-beta is administered before the induction period (i), and/or after the maintenance period (iii).

Another object of the present invention resides in the use of a combination of Cladribine and IFN-beta as disclosed herein, wherein Cladribine is to be orally administered following the sequential steps disclosed herein and wherein IFN-beta is administered during the Cladribine-free period (ii) and/or (iv).

In a preferred embodiment of the present invention IFN-beta is administered simultaneously with oral Cladribine. Therefore, another object of the present invention resides in the use of a combination of Cladribine and IFN-beta as disclosed herein, wherein Cladribine is to be orally administered following the sequential steps disclosed herein and wherein IFN-beta is administered during the induction period (i) and/or the maintenance period (iv). Even more preferably, IFN-beta is administered during the induction period (i), the maintenance period (iv) and the Cladribine-free periods (ii) and (iv). Even more preferably, IFN-beta is administered before the induction period (i), during the induction period (i), during the maintenance period (iv), during the Cladribine-free periods (ii) and (iv) and after the Cladribine-free period (iv).

As disclosed here above, in a preferred embodiment of the present invention the IFN-beta protein is chosen in the group consisting of: interferon-beta 1a, such as for example Avonex® (Biogen) or Rebif® (Serono), and interferon-beta 1b, such as for example Betaseron® (Berlex/Schering AG). Preferably, the IFN-beta to be used in the frame of the present invention is Rebif® (Serono).

IFN-beta is preferably administered systemically, and preferably subcutaneously or intramuscularly. In one embodiment of the present invention the IFN-beta is dosed at least at 44 mcg subcutaneously per administration. Preferred doses and regimens in accordance with the present invention are selected from the group consisting of: 12 MIU (44 mcg) of IFN-beta three times a week, 12 MIU (44 mcg) daily, 24 MIU (88 mcg) three times a week, 24 MIU (88 mcg) daily. These doses are preferably administered subcutaneously. In one particularly preferred embodiment the IFN-beta is dosed at 44 mcg subcutaneously three times a week, preferably in this case the IFN-beta used is Rebif® (Serono).

All patent and literature references cited in the present specification are hereby incorporated by reference in their entirety.

Further aspects and advantages of the present invention will be disclosed in the following examples, which should be considered as illustrative only, and do not limit the scope of this application.

EXAMPLES

The following abbreviations refer respectively to the definitions below:

kg (kilogram), µg (microgram), mg (milligram), AEs (Adverse effects), CNS (Central nervous system), CSF (Cerebrospinal fluid), EDSS (Expanded Disability Status Scale, SNRS (Scripps Neurologic Rating Scale), IFN (interferon), i.v. (intra-veinous), MIU (Million International units), MS (multiple sclerosis), MRI (Magnetic resonance imaging), p.o. (per os), PPMS (Primary progressive multiple sclerosis), PRMS (Progressive relapsing multiple sclerosis), RRMS (Relapsing-remitting multiple sclerosis), SPMS (Secondary progressive multiple sclerosis), s.c. (subcutaneous), TIW (Three times a week), 2-CdA (2-chloro-2'deoxyadenosine or Cladribine), UI (International unit).

The efficacy and safety of oral Cladribine administration, eventually multi-dose administration, and of the administration in combination with IFN-beta, according to the invention can be assessed for example following the protocols below:

Example 1: Oral Cladribine in the Treatment of Relapsing Forms of MS

A study of sixty patients with relapsing forms of clinically definite multiple sclerosis is undertaken. Each patient is first examined for normal hepatic, renal, and bone marrow functioning to establish baseline values.

Patients are selected from Male or Female, between 18 and 55 years of age who had one or more relapses within the prior 12 months. Female patients are non-pregnant female.

Patients are randomly assigned to one of the treatment groups listed in Table 1 below:

TABLE 1

| Group | 2-CdA |
|---|---|
| 1 | — |
| 2 | 1.75 mg/kg |
| 3 | 3.5 mg/kg |

Each of the patients in Groups 2 and 3 receives 3 mg or 10 mg 2-CdA (1, 2 or 3 administration(s) a day depending on the patient's weight) combined in cyclodextrin formulation as described in WO 2004/087101, Example 3. The Compositions of the Cladribine formulations in 3 mg or 10 mg 2-CdA tablets containing hydroxypropyl-beta-cyclodextrin are listed in Table 2 below:

TABLE 2

| Name of ingredients | Formula mg/tablet | Formula mg/tablet |
|---|---|---|
| Cladribine-2-hydroxypropyl-β-cyclodextrin- complex* | 153.75 equivalent to 10 mg 2-CdA | 30.60 equivalent to 3 mg 2-CdA |
| Sorbitol powder | 44.25 | 68.4 |
| Magnesium Stearate (vegetable grade) | 2.0 | 1.00 |
| Total | 200.0 | 100 |

*Cladribine is complexed and lyophilised with 2-hydroxypropyl-β-cyclodextrin as a separate process as described in WO 2004/087101.

Examples of administration schemes for the induction period depending on the patient's weight are given below in Tables 3 and 4 for the target doses of 1.75 mg/kg and 3.5 mg/kg respectively. For the maintenance period, the example of administration scheme of Table 3 is applicable.

TABLE 3

| Patient weight ranges (kg) | | | Total target dose (kg) equivalent to 1.75 mg/kg | | Number of pills (10 mg)/induction period | | |
|---|---|---|---|---|---|---|---|
| Min | Mid range | Max | Min | Max | Month 1 | Month 2 | Total |
| 40 | 42.5 | 44.9 | 28 | 31.4 | 4 | 3 | 7 |
| 45 | 47.5 | 49.9 | 31.5 | 34.9 | 4 | 4 | 8 |
| 50 | 52.5 | 54.9 | 35 | 38.4 | 5 | 4 | 9 |
| 55 | 57.5 | 59.9 | 38.5 | 41.9 | 5 | 5 | 10 |
| 60 | 62.5 | 64.9 | 42 | 45.4 | 5 | 5 | 10 |
| 65 | 67.5 | 69.9 | 45.5 | 48.9 | 6 | 5 | 11 |
| 70 | 72.5 | 74.9 | 49 | 52.4 | 6 | 6 | 12 |
| 75 | 77.5 | 79.9 | 52.5 | 55.9 | 7 | 6 | 13 |
| 80 | 82.5 | 84.9 | 56 | 59.4 | 7 | 6 | 13 |
| 85 | 87.5 | 89.9 | 59.5 | 62.9 | 7 | 7 | 14 |
| 90 | 92.5 | 94.9 | 63 | 66.4 | 8 | 7 | 15 |
| 95 | 97.5 | 99.9 | 66.5 | 69.9 | 8 | 8 | 16 |
| 100 | 102.5 | 104.9 | 70 | 73.4 | 9 | 8 | 17 |
| 105 | 107.5 | 109.9 | 73.5 | 76.9 | 9 | 9 | 18 |
| 110 | 112.5 | 114.9 | 77 | 80.4 | 9 | 9 | 18 |
| 115 | 117.5 | 119.9 | 80.5 | 83.9 | 10 | 9 | 19 |

TABLE 4

| Patient weight ranges (kg) | | | Total target dose (kg) equivalent to 3.5 mg/kg | | Number of pills (10 mg)/induction period | | | | |
|---|---|---|---|---|---|---|---|---|---|
| Min | Mid range | Max | Min | Max | Month 1 | Month 2 | Month 3 | Month 4 | Total |
| 40 | 42.5 | 44.9 | 56 | 62.9 | 4 | 4 | 3 | 3 | 14 |
| 45 | 47.5 | 49.9 | 63 | 69.9 | 4 | 4 | 4 | 4 | 16 |
| 50 | 52.5 | 54.9 | 70 | 76.9 | 5 | 4 | 4 | 4 | 17 |
| 55 | 57.5 | 59.9 | 77 | 83.9 | 5 | 5 | 5 | 4 | 19 |
| 60 | 62.5 | 64.9 | 84 | 90.9 | 6 | 5 | 5 | 5 | 21 |
| 65 | 67.5 | 69.9 | 91 | 97.9 | 6 | 6 | 5 | 5 | 22 |
| 70 | 72.5 | 74.9 | 98 | 104.9 | 6 | 6 | 6 | 6 | 24 |
| 75 | 77.5 | 79.9 | 105 | 111.9 | 7 | 7 | 6 | 6 | 26 |
| 80 | 82.5 | 84.9 | 112 | 118.9 | 7 | 7 | 7 | 6 | 27 |
| 85 | 87.5 | 89.9 | 119 | 125.9 | 7 | 7 | 7 | 7 | 28 |
| 90 | 92.5 | 94.9 | 126 | 132.9 | 8 | 8 | 7 | 7 | 30 |
| 95 | 97.5 | 99.9 | 133 | 139.9 | 8 | 8 | 8 | 8 | 32 |
| 100 | 102.5 | 104.9 | 140 | 146.9 | 9 | 8 | 8 | 8 | 33 |
| 105 | 107.5 | 109.9 | 147 | 153.9 | 9 | 9 | 9 | 8 | 35 |
| 110 | 112.5 | 114.9 | 154 | 160.9 | 10 | 9 | 9 | 9 | 37 |
| 115 | 117.5 | 119.9 | 161 | 167.9 | 10 | 10 | 9 | 9 | 38 |

In Group 1 patients receive a placebo (saline) for 4 months followed by 8 months of no treatment.

In Group 2 patients receive a daily oral administration of Cladribine for about 5 days a month during 2 months (induction period) of 2-CdA cyclodextrin formulation such as the total effective dose administered at the end of the first 2 months approximates about 0.7 mg/kg (total dose of about 1.75 mg/kg for a bioavailability of about 40%); followed by administration of placebo for 2 months; followed by 8 months of no treatment.

In Group 3 patients receive a daily oral administration of Cladribine for about 5 days a month during 4 months (induction period) of 2-CdA cyclodextrin formulation such as the total effective dose administered at the end of the first 4 months approximates about 1.4 mg/kg (total dose of about 3.5 mg/kg for a bioavailablility of about 40%); followed by 8 months of no treatment.

Beginning at month 13, all 3 patient groups receive re-treatment with Cladribine cyclodextrin formulation for about 5 days a month for 2 months (maintenance period) with the lower dose (such as the total effective dose administered at the end of the first 2 months approximates about 0.7 mg/kg) followed by 10 months of no treatment.

Finally, beginning at month 25, all patient groups receive re-treatment with Cladribine cyclodextrin formulation for about 5 days a month for 2 months (maintenance period) with the lower dose (such as the total effective dose administered at the end of the first 2 months approximates about 0.7 mg/kg) followed by 10 more months of no treatment.

Patients are monitored to determine whether there is any progression or improvement of brain lesions associated with progression of MS through MRI scans and neurological examination as described in Miller et al., 1996, above; Evans et al., 1997, above; Sipe et al., 1984, above; and Mattson, 2002, above. All patients have a baseline and MRI study (brain or spinal cord, according to localization of the lesions) at month 12.

The patient's disability progression and the time for having a first relapse are monitored as well as the proportion of relapse-free patients at 24 months.

Lymphocyte markers and monocyte counts are monitored in the patients.

Patients in Groups 2 and 3 have a decrease in brain lesions.

The data show that the 2-CdA regimen consisting in the succession of an induction treatment and maintenance treatments is efficient in decreasing brain lesions and no severe adverse effect is observed.

Example 2: Combination Treatment of Oral Cladribine and Rebif® in the Treatment of MS 1. Patients A study of two hundred and twenty (220) patients with relapsing form of clinically definite MS and who have experienced at least one relapse in the preceding 48 weeks prior to screening while taking Rebif® is undertaken.

To qualify for enrollment in this 96-weeks treatment study, subjects have:

experienced at least one relapse within the previous 48 weeks (prior to Screening) and;

been receiving Rebif® for at least 48 weeks prior to Screening.

Patients are selected from male or female, 18-55 years of age (inclusive), weight between 40-120 kg, inclusive.

Once enrolled, these subjects experiencing active MS symptoms while taking Rebif® are randomized in a 2:2:1 ratio to receive high dose cladribine (N=89, defined as Group 3, see table 1), low dose cladribine (N=89; defined as Group 2, see table 1) or placebo (N=42; defined as Group 1, see table 1) add-on to their existing Rebif® regimen.

For this study, subjects receiving placebo as add-on therapy to their existing Rebif® regimen are the control group. Subjects' responses to add-on cladribine to Rebif® therapy, with respect to safety, tolerability, and efficacy, are compared to subjects' responses to placebo add-on to Rebif® therapy.

2. Products

Subjects entering the study are provided with Cladribine presented in 10 mg tablets in a complex with 2-hydroxy-propyl-β-cyclodextrin (see Table 2), and Rebif®.

Rebif® is supplied as a sterile solution in ready-to-use pre-filled syringe at 44 mcg (0.5 mL volume), intended for subcutaneous administration.

The dosage of Rebif® is 44 mcg injected subcutaneously three times per week.

Cladribine is presented in tablets containing 10 mg of cladribine in a complex with 2-hydroxypropyl-β-cyclodextrin (see Table 2).

The matching placebo tablets have the same composition as the cladribine tablets but do not contain cladribine. For placebo, cladribine is replaced by 10 mg of 2-hydroxypropyl-β-cyclodextrin.

3. Administration Scheme

Dose:

Cladribine is administered orally in 10 mg tablets. The number of tablets to be administered is standardized based on weight, using 10 kg weight ranges (i.e. 60-69.9 kg, 70-79.9 kg, etc.; see table 7), dispensed in blister packs ranging from four to ten tablets, depending on the weight range and treatment arm to which a subject is randomized.

The total number of tablets dispensed in a blister pack should be administered evenly over a 4-5 day period. For example, a subject who receives five tablets should take one a day for five days; whereas a subject who receives seven tablets should take two on Day 1, two on Day 2, one on Day 3, one on Day 4 and one on Day 5 (see table 5).

Table 5 illustrates the breakdown of daily tablet administration for one cycle of treatment.

TABLE 5

Daily Cladribine tablet Administration for one cycle of treatment

| Total # of Tablets Dispensed | Day 1 | Day 2 | Day 3 | Day 4 | Day 5 |
|---|---|---|---|---|---|
| 4 | 1 | 1 | 1 | 1 | 0 |
| 5 | 1 | 1 | 1 | 1 | 1 |
| 6 | 2 | 1 | 1 | 1 | 1 |
| 7 | 2 | 2 | 1 | 1 | 1 |
| 8 | 2 | 2 | 2 | 1 | 1 |
| 9 | 2 | 2 | 2 | 2 | 1 |
| 10 | 2 | 2 | 2 | 2 | 2 |

Patients who receive Cladribine receive it during two periods. The first period is named the induction period and the second period is named the maintenance period.

TABLE 6

Type of Cladribine Tablets Per CYCLE and By Treatment Arm

| Arm | Cycle 1 Day 1 | Cycle 2 Wk 5 | Cycle 3 Wk 9 | Cycle 4 Wk 13 | Yearly cumulative dose (Induction Treatment) | Cycle 5 Wk 48 | Cycle 6 Wk 52 | Yearly cumulative dose (maintenance) | Total Cumulative Dose (Induction and Maintenance) |
|---|---|---|---|---|---|---|---|---|---|
| Placebo | Placebo | Placebo | Placebo | Placebo | 0 mg/kg | Placebo | Placebo | 0 mg/kg | 0 mg/kg |
| Low Dose | Active | Active | Placebo | Placebo | 1.75 mg/kg | Active | Active | 1.75 mg/kg | 3.5 mg/kg |
| High Dose | Active | Active | Active | Active | 3.5 mg/kg | Active | Active | 1.75 mg/kg | 5.25 mg/kg |

Induction Period (Weeks 5, 9, 13)

The first 48 weeks correspond to the induction period (start of Study Day 1 through end of Week 47). The three groups of patients follow the following scheme (see table 6):

Group 3 (High-dose Cladribine) receive 0.875 mg/kg/ cycle for four consecutive cycles;

Group 2 (Low-dose Cladribine) receive 0.875 mg/kg/ cycle for two consecutive cycles+placebo for two cycles;

Group 1 (Placebo) receive placebo for four consecutive cycles.

Following the initial course of treatment dispensed at Study Day 1, each subject return for three additional treatments, at four-week intervals, at the start of Weeks 5, 9, and 13 (see table 6).

Since accurate drug dosing of cladribine/placebo is based on weight, prior to dispensing cladribine/placebo tablets at the start of Weeks 5, 9 and 13, the subject's weight should be accurately assessed.

All the patients receive low-dose or high-dose cladribine tablets or placebo as an "add-on" to their ongoing Rebif® treatment regimen during the induction period.

Maintenance Period (Weeks 48 and 52)

In the maintenance period (Weeks 48 through 96), subjects who received cladribine in the induction period then receive low-dose cladribine (0.875 mg/kg/cycle for two cycles, see table 6), added to Rebif®, while those who received placebo continue to receive placebo (for two cycles see table 6), added to Rebif®.

The tablets of Cladribine are 10 mg in strength and are dispensed, based on standardized 10 kg weight ranges (see table 7). Each treatment cycle are defined as individual daily oral doses of cladribine tablets administered for 4-5 consecutive days (see table 5) during a 28-day period.

TABLE 7

Number of Cladribine Tablets Per cycle And Per Weight Group

High Dose (0.875 mg/kg/ cycle for 4 cycles)

| Weight Ranges | | | Number of Tablets/Cycle (Treatment) | | | | Active Tablets | Placebo Tablets | Total Tablets | Number of Tablets/Cycle (Retreatment) | | Active Tablets | Placebo Tablets | Total Tablets |
|---|---|---|---|---|---|---|---|---|---|---|---|---|---|---|
| Min | Mid Range | Max | Cycle 1 | Cycle 2 | Cycle 3 | Cycle 4 | | | | Cycle 1 | Cycle 2 | | | |
| 40 | 45 | 49.9 | 4 | 4 | 4 | 4 | 16 | | 16 | 4 | 4 | 8 | | 8 |
| 50 | 55 | 59.9 | 5 | 5 | 5 | 5 | 20 | | 20 | 5 | 5 | 10 | | 10 |
| 60 | 65 | 69.9 | 6 | 6 | 6 | 5 | 23 | | 23 | 6 | 6 | 12 | | 12 |
| 70 | 75 | 79.9 | 7 | 7 | 7 | 6 | 27 | | 27 | 7 | 7 | 14 | | 14 |
| 80 | 85 | 89.9 | 8 | 7 | 8 | 7 | 30 | | 30 | 8 | 7 | 15 | | 15 |
| 90 | 95 | 99.9 | 9 | 8 | 9 | 8 | 34 | | 34 | 9 | 8 | 17 | | 17 |
| 100 | 105 | 109.9 | 10 | 9 | 9 | 9 | 37 | | 37 | 10 | 9 | 19 | | 19 |
| 110 | 115 | 119.9 | 10 | 10 | 10 | 10 | 40 | | 40 | 10 | 10 | 20 | | 20 |

Low Dose (0.875 mg/kg/ cycle for 2 cycles + placebo for 2 cycles)

| Weight Ranges | | | Number of Tablets/Cycle (Treatment) | | | | Active Tablets | Placebo Tablets* | Total Tablets | Number of Tablets/Cycle (Retreatment) | | Active Tablets | Placebo Tablets | Total Tablets |
|---|---|---|---|---|---|---|---|---|---|---|---|---|---|---|
| Min | Mid Range | Max | Cycle 1 | Cycle 2 | Cycle 3 | Cycle 4 | | | | Cycle 1 | Cycle 2 | | | |
| 40 | 45 | 49.9 | 4 | 4 | *4* | *4* | 8 | *8* | 16 | 4 | 4 | 8 | | 8 |
| 50 | 55 | 59.9 | 5 | 5 | *5* | *5* | 10 | *10* | 20 | 5 | 5 | 10 | | 10 |
| 60 | 65 | 69.9 | 6 | 6 | *6* | *5* | 12 | *11* | 23 | 6 | 6 | 12 | | 12 |
| 70 | 75 | 79.9 | 7 | 7 | *7* | *6* | 14 | *13* | 27 | 7 | 7 | 14 | | 14 |
| 80 | 85 | 89.9 | 8 | 7 | *8* | *7* | 15 | *15* | 30 | 8 | 7 | 15 | | 15 |
| 90 | 95 | 99.9 | 9 | 8 | *9* | *8* | 17 | *17* | 34 | 9 | 8 | 17 | | 17 |

TABLE 7-continued

Number of Cladribine Tablets Per cycle And Per Weight Group

| 100 | 105 | 109.9 | 10 | 9  | *9*  | *9*  | 19 | *18* | 37 | 10 | 9  | 19 | | 19 |
| --- | --- | ----- | -- | -- | ---- | ---- | -- | ---- | -- | -- | -- | -- |-| -- |
| 110 | 115 | 119.9 | 10 | 10 | *10* | *10* | 20 | *20* | 40 | 10 | 10 | 20 | | 20 |

Placebo (4 cycles)

| Weight Ranges | | | Number of Tablets/Cycle (Treatment) | | | | Active | Placebo | Total | Number of Tablets/Cycle (Retreatment) | | Active | | Total |
|---|---|---|---|---|---|---|---|---|---|---|---|---|---|---|
| Min | Range | Max | Cycle 1 | Cycle 2 | Cycle 3 | Cycle 4 | Tablets | Tablets* | Tablets | Cycle 1 | Cycle 2 | Tablets | Placebo Tablets* | Tablets |
| 40  | 45  | 49.9  | *4*  | *4*  | *4*  | *4*  | | *16* | 16 | *4*  | *4*  | | *8*  | 8  |
| 50  | 55  | 59.9  | *5*  | *5*  | *5*  | *5*  | | *20* | 20 | *5*  | *5*  | | *10* | 10 |
| 60  | 65  | 69.9  | *6*  | *6*  | *6*  | *5*  | | *23* | 23 | *6*  | *6*  | | *12* | 12 |
| 70  | 75  | 79.9  | *7*  | *7*  | *7*  | *6*  | | *27* | 27 | *7*  | *7*  | | *14* | 14 |
| 80  | 85  | 89.9  | *8*  | *7*  | *8*  | *7*  | | *30* | 30 | *8*  | *7*  | | *15* | 15 |
| 90  | 95  | 99.9  | *9*  | *8*  | *9*  | *8*  | | *34* | 34 | *9*  | *8*  | | *17* | 17 |
| 100 | 105 | 109.9 | *10* | *9*  | *9*  | *9*  | | *37* | 37 | *10* | *9*  | | *19* | 19 |
| 110 | 115 | 119.9 | *10* | *10* | *10* | *10* | | *40* | 40 | *10* | *10* | | *20* | 20 |

*Placebo tablets are in bold italic underlined.

The study is designed to evaluate the safety, tolerability and efficacy of oral Cladribine when added to Rebif® in multiple sclerosis subjects with active disease compared to placebo when added to Rebif® in the same population of subjects.

In particular, the sample size for this study is designed to detect a reduction in the mean number of $T_1$ gadolinium-enhanced lesions per subject after 96 weeks of Rebif® plus Cladribine compared to Rebif® plus placebo add-on therapy in subjects who had at least one relapse while taking Rebif® in the 48 weeks prior to entering this study.

Lymphocyte markers and monocyte counts are monitored in the patients.

Patients are monitored to determine whether there is any progression or improvement of brain lesions associated with progression of MS through MRI scans and neurological examination as described in Miller et al., 1996, above; Evans et al., 1997, above; Sipe et al., 1984, above; and Mattson, 2002, above.

The patient's disability progression and the time for having a first relapse are monitored as well as the proportion of relapse-free patients at 24 months.

The efficacy of the treatment is measured by the frequency of relapses in RRMS and the monitoring of the lesions in the CNS as detected using methods such as MRI technique (Miller et al., 1996, *Neurology*, 47(Suppl 4): S217; Evans et al., 1997, *Ann. Neurology*, 41:125-132).

The observation of the reduction and/or suppression of MRI $T_1$ gadolinium-enhanced lesions (thought to represent areas of active inflammation) gives a primary efficacy variable.

Secondary efficacy variables include number of combined active lesions per subject defined as new T1 gadolinium-enhancing, or new T2 non-enhancing, or enlarging lesions, or both (without double-counting); number of active T2 lesions per subject; number of active T1 gadolinium-enhanced lesions per subject; proportion of subjects with no active T2 lesions; proportion of subjects with no active T1 gadolinium-enhanced lesions; change in T2 lesion volume; relapse rate; Expanded Disability Status Scale score and Scripps Neurologic Rating Scale (SNRS) score (Sipe et al., 1984, *Neurology*, 34, 1368-1372).

Patients in Groups 2 and 3 have a decrease in brain lesions.

The data show that the 2-CdA regimen consisting in the succession of an induction treatment and maintenance treatments combined with a treatment with Rebif® is efficient in decreasing brain lesions of and no severe adverse effect is observed.

A follow up extension study for an additional 48 weeks duration at the conclusion of this 96-week trial is possible. The follow-up extension study dosing starts with the Week 96. Subjects receive Cladribine 1.75 mg/kg/year provided over 2 cycles+Rebif® 44 mcg TIW following the same scheme as the maintenance period described here above.

The invention claimed is:
1. A method of treating patients suffering from multiple sclerosis and who are refractory to at least one conventional therapy for multiple sclerosis with interferon beta-1a, interferon beta-1b, or glatiramer acetate, said method comprising administering IFN-β in combination with orally administered Cladribine to a patient refractory to at least one conventional therapy for multiple sclerosis with interferon beta-1a, interferon beta-1b, or glatiramer acetate according to the following sequential steps:
   (i) an induction period wherein Cladribine is administered and wherein the total dose of Cladribine reached at the end of the induction period is from about 1.5 mg/kg to about 3.5 mg/kg;
   (ii) a Cladribine-free period wherein no Cladribine is administered;
   (iii) a maintenance period wherein Cladribine is administered and wherein the total dose of Cladribine administered during the maintenance period is lower than or equal to the total dose of Cladribine reached at the end of the induction period (i); and
   (iv) a Cladribine-free period wherein no Cladribine is administered;
wherein the combined duration of the induction period (i) with the Cladribine-free period (ii) is about 1 year and:
a) the duration of the induction period (i) is about 4 months and the duration of the Cladribine-free period (ii) is about 8 months;
b) the duration of the induction period (i) is about 2 months and the duration of the Cladribine-free period (ii) is about 10 months; or
c) the duration of the induction period (i) is up to 4 months and the duration of the Cladribine-free period (ii) is up to 8 months.

2. The method according to claim 1, wherein the total dose of Cladribine reached at the end of the induction period (i) is from about 1.7 mg/kg to about 3.5 mg/kg.

3. The method according to claim 1, wherein the combined duration of the induction period (i) with the Cladribine-free period (ii) is about 1 year and the total dose of Cladribine reached at the end of this year of treatment is about 1.7 mg/kg or about 3.5 mg/kg.

4. The method according to claim 1, wherein the combined duration of the maintenance period (iii) with the Cladribine-free period (iv) is about 1 year.

5. The method according to claim 4, wherein the duration of the maintenance period (iii) is about 2 months and the duration of the Cladribine-free period (iv) is about 10 months.

6. The method according to claim 4, wherein the combined duration of the maintenance period (iii) with the Cladribine-free period (iv) is about 1 year and the total dose of Cladribine administered during this year of treatment is about 1.7 mg/kg.

7. The method according to claim 1, wherein the combined duration of the induction period (i), the Cladribine-free period (ii), the maintenance period (iii) and the Cladribine-free period (iv) is about 2 years.

8. The method according to claim 7, wherein:
the duration of the induction period (i) is about 4 months, the duration of the Cladribine-free period (ii) is about 8 months, the duration of the maintenance period (iii) is about 2 months and the duration of the Cladribine-free period (iv) is about 10 months; or
the duration of the induction period (i) is about 2 months, the duration of the Cladribine-free period (ii) is about 10 months, the duration of the maintenance period (iii) is about 2 months and the duration of the Cladribine-free period (iv) is about 10 months.

9. The method according to claim 7, wherein the combined duration of the induction period (i) and the Cladribine-free period (ii) is about 1 year, the combined duration of the maintenance period (iii) and the Cladribine-free period (iv) is about 1 year, the total dose of Cladribine administered during the first year of treatment is about 1.7 mg/kg and the total dose of Cladribine administered during the second year of treatment is about 1.7 mg/kg.

10. The method according to claim 7, wherein the combined duration of the induction period (i) and the Cladribine-free period (ii) is about 1 year, the combined duration of the maintenance period (iii) and the Cladribine-free period (iv) is about 1 year, the total dose of Cladribine administered during the first year of treatment is about 3.5 mg/kg and the total dose of Cladribine administered during the second year of treatment is about 1.7 mg/kg.

11. The method according to claim 1, wherein steps (iii) to (iv) are repeated one, two or three times.

12. The method according to claim 1, wherein the bioavailability of Cladribine is about 40%.

13. The method according to claim 1, wherein the total effective dose of Cladribine reached at the end of the induction period (i) is about 0.7 mg/kg or about 1.4 mg/kg.

14. The method according to claim 1, wherein the total effective dose of Cladribine administered during the maintenance period (iii) is about 0.7 mg/kg.

15. The method according to claim 1, wherein Cladribine is administered from 4 to 7 days per month during the induction period (i).

16. The method according to claim 15, wherein Cladribine is administered from day 1 to day 5 each month during the induction period (i).

17. The method according to claim 15, wherein Cladribine is administered at a daily dose of about 0.175 mg/kg during the induction period (i).

18. The method according to claim 1, wherein Cladribine is administered from 4 to 7 days per month during the maintenance period (iii).

19. The method according to claim 18, wherein Cladribine is administered from day 1 to day 5 each month during the maintenance period (iii).

20. The method according to claim 18, wherein Cladribine is administered at a daily dose of about 0.175 mg/kg during the maintenance period (iii).

21. The method according to claim 1, wherein IFN-beta is administered simultaneously, separately or sequentially with oral Cladribine.

22. The method according to claim 21, wherein IFN-beta is administered simultaneously with oral Cladribine.

23. The method according to claim 22, wherein IFN-beta is administered during the induction period (i), the maintenance period (iii) and the Cladribine-free periods (ii) and (iv).

24. The method according to claim 23, wherein IFN-beta is administered before the induction period (i), during the induction period (i), during the maintenance period (iii), during the Cladribine-free periods (ii) and (iv) and after the Cladribine-free period (iv).

25. The method according to claim 21, wherein the IFN-beta is administered subcutaneously or intramuscularly.

26. The method according to claim 25, wherein the IFN-β is administered at 44 mcg subcutaneously three times a week.

27. The method according to claim 1, wherein the conventional therapy is selected from the group consisting of:

treatment with treatment with Glatiramer Acetate, treatment with natalizumab, and treatment with Mitoxantrone.

28. The method according to claim 1, wherein the conventional therapy is treatment with beta interferon.

29. The method according to claim 1, wherein the refractory patients to be treated have experienced at least one relapse in spite of receiving at least one conventional therapy.

30. The method according to claim 29, wherein the at least one relapse occurred during the year prior the beginning of the treatment.

31. The method according to claim 30, wherein the patients to be treated have experienced at least one relapse during the year preceding the beginning of the treatment and have been treated with 12 MIU (44 mcg) of IFN-β three times a week.

32. The method according to claim 1, wherein the refractory patients to be treated have acquired enhanced lesion number or enhanced brain lesion volume in the CNS as detected using methods such as MRI technique.

33. The method according to claim 32, wherein the enhanced lesion number or enhanced brain lesion volume occurred during the year prior to the beginning of the treatment.

34. The method according to claim 33, wherein the patients to be treated have acquired enhanced lesion number or enhanced brain lesion volume in the CNS during the year.

35. The method according to claim 1, wherein the refractory patients to be treated have experienced at least one relapse and have developed increasing disability because of progressive forms of the disease.

36. The method according to claim 1, wherein the refractory patients to be treated are suffering from worsening MS, secondary progressive MS, progressive remitting MS or worsening relapsing-remitting MS.

37. The method according to claim 1, wherein the combined duration of the induction period (i) with the Cladribine-free period (ii) is about 1 year and the duration of the induction period (i) is about 2 months and the duration of the Cladribine-free period (ii) is about 10 months.

38. The method according to claim 1, wherein the combined duration of the induction period (i) with the Cladribine-free period (ii) is about 1 year and the duration of the induction period (i) is up to 4 months and the duration of the Cladribine-free period (ii) is up to 8 months.

39. The method according to claim 1, wherein the combined duration of the induction period (i) with the Cladribine-free period (ii) is 1 year and the duration of the induction period (i) is 4 months and the duration of the Cladribine-free period (ii) is 8 months.

40. The method according to claim 1, wherein said IFN-β is IFN-β1a or IFN-β1b.

* * * * *